United States Patent [19]

Cavalla et al.

[11] 4,029,801

[45] June 14, 1977

[54] PHARMACEUTICAL COMPOSITIONS AND METHODS OF TREATING HYPERTENSION

[75] Inventors: John Frederick Cavalla, Isleworth; John Leheup Archibald, Windsor, both of England

[73] Assignee: John Wyeth & Brother Limited, Maidenhead, England

[22] Filed: Apr. 2, 1975

[21] Appl. No.: 564,508

Related U.S. Application Data

[63] Continuation-in-part of Ser. No. 323,684, Jan. 15, 1973, abandoned, which is a continuation-in-part of Ser. No. 175,345, Aug. 26, 1971, abandoned.

[30] Foreign Application Priority Data

Sept. 3, 1970 United Kingdom ............. 42090/70
July 22, 1971 United Kingdom ............. 34376/71

[52] U.S. Cl. ............................. 424/267; 424/258; 424/263
[51] Int. Cl.$^2$ ...................................... A61K 31/445
[58] Field of Search ............... 424/267; 260/293.77

[56] References Cited

OTHER PUBLICATIONS

Harper et al., J. Med. Chem., vol. 7: 729–732, (1964).

*Primary Examiner*—Leonard Schenkman
*Attorney, Agent, or Firm*—Arthur E. Wilfond

[57] ABSTRACT

Pharmaceutical compositions containing a group of heterocyclic compounds and their use in treatment of disorders and diseases of the cardiovascular system and/or in the treatment of superficial and deep allergic phenomena is described. These compounds used in the composition and/or methods are piperidine compounds linked by the nitrogen atom to a substituted or unsubstituted cycloalkyl, aryl or heterocyclic radical through the intermediary of a group selected from a lower-alkylene radical, a monoketo lower-alkylene radical or a hydroxy-lower-alkylene radical, or a bivalent radical of the formula —NH.CO.(CH$_2$)$_n$— where $n$ is 1, 2 or 3,

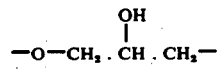

or —O-(lower-alkylene)—. The piperidine ring is further substituted by an acylamino residue.

16 Claims, No Drawings

PHARMACEUTICAL COMPOSITIONS AND METHODS OF TREATING HYPERTENSION

This application is a continuation-in-part of our copending application Ser. No. 323,684 filed Jan. 15, 1973, now abandoned, and entitled "heterocyclic Compounds" which is a continuation-in-part of our application Ser. No. 175,345 filed Aug. 26, 1971 entitled "Pharmaceutical Compositions" and now abandoned.

This invention relates to pharmaceutical compositions containing heterocyclic compounds and to the use of some of the heterocyclic compounds in a method of treating disorders and diseases of the cardiovascular system and/or deep superficial allergic phenomena in mammals.

The invention provides a pharmaceutical composition comprising a non-toxic pharmaceutically acceptable carrier and an effective amount of a heterocyclic compound of general formula (Ia)

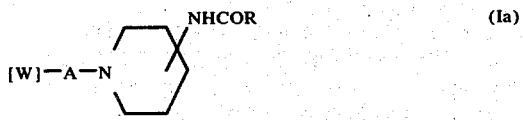

wherein W represents a cycloalkyl radical containing five to seven ring carbon atoms, a carbocyclic aryl radical, or a heterocyclic radical selected from pyridyl, pyrrolyl, imidazolyl, quinolyl, benzthienyl, benzodioxanyl, benzindolyl, and radicals of the formula $Ar_2CHCH_2$— and $Ar_2C=CH$—, wherein Ar is a phenyl radical, all of which W radicals may be substituted or unsubstituted, A represents a lower alkylene radical, a monoketo lower alkylene radical, a hydroxy-lower-alkylene radical or a bivalent radical of the formula —NH—CO$(CH_2)_n$, —O—$CH_2CH(OH)CH_2$— or —O—(lower alkylene)—, R represents a substituted or unsubstituted phenyl radical or a cycloalkyl radical containing from 5 to 7 ring carbon atoms, n is the integer 1, 2 or 3, the term "lower" means that the radical contains from 1 to 6 carbon atoms, and the pharmaceutically acceptable acid addition salts thereof with the proviso that when W is $Ar_2CHCH_2$— or ArC:CH— then A is a lower alkylene radical of 1 to 4 carbon atoms.

It is to be understood that the term "alkylene" used herein includes both straight and branched chain radicals, the term "lower" means the radical concerned contains 1 to 6 carbon atoms, preferably 1 to 4 carbon atoms, and by the term "aryl" radical is meant a radical possessing aromatic character.

The compounds of formula (Ia) wherein W and A are as defined above, R represents a substituted or unsubstituted phenyl radical or a cycloalkyl radical containing 5 to 7 ring carbon atoms, and the pharmaceutically acceptable acid addition salts thereof and wherein the proviso above applies, exhibit pharmacological activity for example one or more of the following activities:

action on the cardiovascular system (such as hypotensive and/or anti-hypertensive and/or peripheral vasodilation and/or anti-anginal and/or anti-arrhythmic activity), anti-histamine activity such as activity against superficial and deep allergic phenomena for example, Urticaria, Pruritus, Allergic Rhinitis, Anaphylactic shock and Asthma, and sometimes central nervous system activity (such as sedative or anti-convulsant activities) and anti-inflammatory activity when tested on warm-blooded animals. Most of the active compounds which have been prepared and tested have been found to possess action on the cardiovascular system.

Generally the compounds used in the pharmaceutical compositions and treatment methods of this invention are novel compounds.

However, certain compounds wherein W is an unsubstituted phenyl radical and A is —$CH_2$— or —$CH_2CH_2$— are known compounds having been described by Harper and Chignell, J.Med.Chem., 1964, 7, 729–732. These known compounds were employed by Harper & Chignell as chemical intermediates for other compounds which were tested for CNS and analgesic activity.

In addition to having useful pharmaceutical properties as mentioned above the novel compounds of the invention are intermediates for the preparation of other compounds of formula Ia.

A preferred group of compounds for use in the pharmaceutical compositions of the invention comprises those of formula Ia wherein W is cyclohexyl, phenyl, monohalophenyl, dihalophenyl, lower alkoxyphenyl, diloweralkoxyphenyl, triloweralkoxyphenyl, lower alkylphenyl, di-(loweralkyl)phenyl, hydroxyphenyl, dihydroxyphenyl, methylenedioxyphenyl, ethylenedioxyphenyl, lower alkanoylaminophenyl, nitrophenyl, aminophenyl, di-(loweralkyl)aminophenyl, or acetylaminohydroxyphenyl, A is lower alkylene of 1 to 6 preferably 2 – 4 carbon atoms or W—A is $Ar_2CHCH_2(CH_2)_n$ or $Ar_2C=CH_2(CH_2)_n$ where Ar is phenyl or halophenyl and n is an integer from 1 to 4.

The invention includes the compounds of this group where W is cyclohexyl or substituted phenyl per se.

The compounds of formula Ia form part of a larger group of compounds of formula I

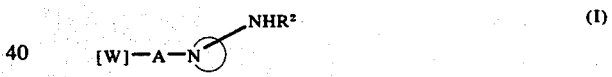

wherein

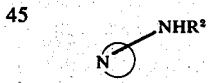

represents a ring system of formula

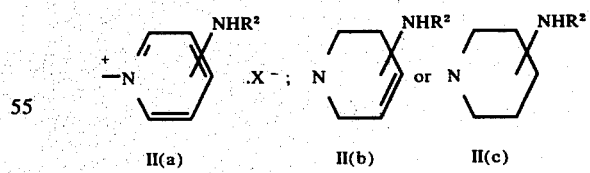

wherein W and A are as herein defined and $R^2$ is hydrogen or the group COR, where R represents a substituted or unsubstituted phenyl radical or a cycloalkyl radical containing from 5 to 7 ring carbon atoms.

Examples of W are unsubstituted phenyl or phenyl substituted by one or more groups, which may be the same or different selected from halogen (for example fluorine, chlorine or bromine), lower alkyl (for example methyl, ethyl, propyl, or n, s and t-butyl), lower alkoxy (for example methoxy, ethoxy, propoxy or butoxy), nitro, amino (including alkyl or dialkyl substituted amino groups) in particular dialkylamino (for example dimethylamino or diethylamino), acylamino in particular alkanoylamino [for example acetylamino (acetamido)], hydroxyl, carboxyl, lower alkoxycarbonyl, alkylenedioxy (for example methylenedioxy), trihaloalkyl (for example trifluromethyl), mercapto, methylthio, methylsulphonyl, phenyl and phenyl substituted by one or more of those substituents mentioned immediately above in connection with the substituted phenyl group W.

When W is the group $Ar_2C:CH-$ or $Ar_2CHCH_2-$ Ar may be any of the substituted or unsubstituted phenyl radicals already mentioned for W when a phenyl radical.

Further examples of W are cycloalkyl (for example cyclohexyl), 1,2,3,4-tetrahydro-naphthyl (for example 1,2,3,4-tetrahydronaphth-6-yl), naphthyl and indenyl radicals which may be unsubstituted or substituted as described above for the substituted phenyl group W, and heterocyclic radicals such as benzo[b]thienyl (for example 3-benzo[b]thienyl), pyrrolyl (for example 2- and 3-pyrrolyl), imidazolyl (for example 4-imidazolyl)], pyridyl (for example 2- and 4-pyridyl), quinolyl (for example 2-quinolyl), benzo-1,4-dioxanyl (for example benzo-1,4-dioxan-2-yl) and benzindolyl in particular benz[g]indolyl (for example 3-benz[g]indolyl), which heterocyclic radicals may be unsubstituted or substituted as described above for the substituted phenyl group W. Examples of A are methylene, ethylene, propylene, methylethylene, butylene oxoethylene, oxalyl, oxo-butylene, hydroxyethylene and hydroxybutylene. Examples of R are the same substituted and unsubstituted phenyl radicals as those already described for the radical W and also cyclopentyl, cyclohexyl and cycloheptyl. Examples of acid addition salts are those formed from inorganic and organic acids in particular pharmaceutically acceptable acid addition salts such as the sulphate, hydrochloride, hydrobromide, hydro-iodide, nitrate, phosphate, sulphonate (such as the methane-sulphonate and p-toluene-sulphonate), acetate, maleate, fumarate, tartrate and formate.

The compounds of general formula (I) can be prepared in a number of ways by building up the molecule from suitable starting materials in known manner. Such processes applied to the preparation of the novel compounds of formula (I) are included in the scope of the invention.

One method of preparation of compounds of general formula (I) in which $R^2$ is the $-COR$ group comprises reacting a compound of the general formula

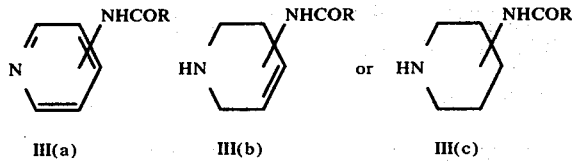

with an alkylating or acylating agent of the general formula

[W]—A—Y          (IV)

wherein R, W and A have the meanings already defined and Y is a halogen atom or an equivalent replaceable atom or radical, for example an organic sulphonyl radical such as tosyl radical. As an alternative, the compounds of formula III(b) or III(c) may be reacted with (i) a compound of the formula

[W]—A¹—H          (V)

wherein the chain $A^1$ contains an epoxide residue for example

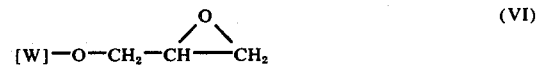

to give a compound of formula (I) wherein the chain A is substituted by a hydroxyl radical, or (ii) a vinyl substituted compound of formula

[W]—B          (VII)

wherein B is a straight or branched chain alkenyl radical, preferably a vinyl radical to give a corresponding compound of formula (I) wherein A is a straight or branched chain alkylene radical, W being other than $Ar_2C:CH$ or $Ar_2CHCH_2-$.

The compounds of general formulae (IV), (V), (VI) and (VII) are known compounds or can be made following the methods known for preparing compounds of these types. The starting materials of general formulae III(a), III(b) and III(c) can generally be made by acylating a corresponding amino compound of the general formula

and if necessary reducing the ring system to the corresponding tetrahydropyridine or piperidine ring. The starting material of general formula III(c) is preferably prepared by either (i) forming the oxime of an N-benzyl-4-piperidone, reducing to give the 4-amino compound, acylating the amino group and then hydrogenolysing the benzyl residue, or (ii) treating the pyridine of formula

with a benzyl halide, for example benzyl chloride to give the quaternary salt, reducing with an alkali metal borohydride to give the corresponding N-benzyl-tetrahydro-pyridine which is further subjected to concomitant de-benzylation and reduction of the 3,4-double bond by catalytic hydrogenation, or (iii) catalytic hydrogenation of compound (IX) in the presence of acetic anhydride to give

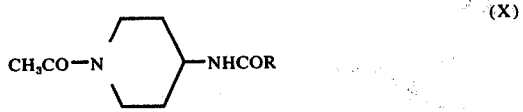

and then selectively hydrolysing the acetyl group.

A second general method of preparation of compounds of formula (I) in which $R^2$ is the —COR group, comprises reacting a compound of formula (I) in which $R^2$ is a hydrogen atom, with either a reactive derivative of an acid of general formula R.COOH (where R is aryl, or cycloalkyl). As a reactive derivative of the acid of formula R.COOH used in the process described above, we have found it preferable usually to use a halide (for example the chloride or bromide) or an anhydride. Other examples of reactive derivatives of the acid R.COOH which may be used are the acid azide, mixed anhydrides and active esters. Furthermore, the compounds of formula (I) in which $R^2$ is the —COR group may also be prepared by treating a compound of formula (I) in which $R^2$ is a hydrogen atom with the acid R.COOH in the presence of a known condensing agent (for example, a carbodiimide), or by first activating the amino function (for example, by forming the phosphazo derivative) and then reacting with the acid R.COOH. In connection with the introduction of the —COR group into a compound of formula (I) in which $R^2$ is a hydrogen atom, reference may be made to "Chemistry of the Amino Acids" by Greenstein and Winitz (John Wiley & Sons. Inc., Publishers, 1961) at pages 782–883 and 943–1108.

When the compounds of general formula (I) are desired in which

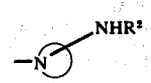

represents a ring system of formula II(b) or II(c), $R^2$ is the —COR group and A is a lower alkylene or a mono- or di-keto lower alkylene radical the preparation may comprise a Mannich reaction using formaldehyde, a compound of formula III(b) or III(c) as secondary amine and either a compound WH, where W has the meanings already defined (except $Ar_2C:CH—$ and $Ar_2CHCH_2—$) and thus WH can be considered as a compound formed by addition of a hydrogen atom to said radical W; said compound WH also containing a suitable reactive site of the type known in the literature to participate in the Mannich reaction, or a derivative of W (as just defined) in which the chain A has already been partially formed, and which partially formed chain contains a site of the type known in the literature to participate in the Mannich reaction. Examples of the latter type of derivative are [W]—$CH_3$ and [W]—$CO.CH_3$ which derivatives are known compounds or can be made following the methods known for preparing compounds of these types. The formaldehyde used in the above reaction may be in the form of a solution in an inert solvent or as paraformaldehyde.

The tetrahydropyridine and piperidine compounds of general formula (I) in which

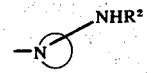

is a ring system of formula II(b) or II(c), $R^2$ is the —COR group and W is other than $Ar_2C:CH—$ or $Ar_2CHCH_2$ may be prepared by starting with a compound of formula

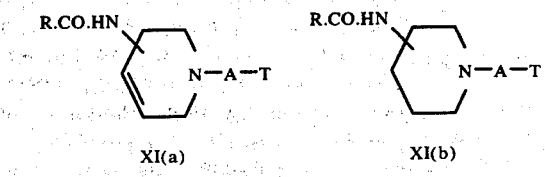

wherein T is a known precursor group of W and reacting with another molecule of the type known in the literature for the formation of W. Reference may be made in this connection to standard textbooks of Organic Chemistry such as: Organic Chemistry by Paul Karrer (Elsevier Publishing Company, Inc., 1950); Organic Chemistry by Fieser & Fieser (Reinhold Publishing Corporation, 1956); Chemistry of Carbon Compounds by Rodd (Elsevier), Amsterdam, 1951–1969); Heterocyclic Compounds edited by Elderfield (John Wiley & Sons, Inc., 1950–1968); and Chemistry of the Heterocyclic Compounds edited by Weissberger (Interscience, 1954). As examples of T may be mentioned —COOAlkyl, —CO.$CH_2$.OH and —$CH_2$.CH(OAlkyl)$_2$ where Alkyl represents a lower alkyl radical. As examples of reactants known to react with T may be mentioned, o-phenylenediamine, 1-naphthylhydrazine or a mixture of formaldehyde and ammonia. The compounds of formula XI(a) and XI(b) may be made following methods known in the art for preparation of similar compounds.

When it is desired to prepared a compound of general formula (I) wherein $R^2$ is a hydrogen atom, a corresponding compound of formula

(wherein W, has the meaning defined in connection with formula (I),

represents a ring system of formula

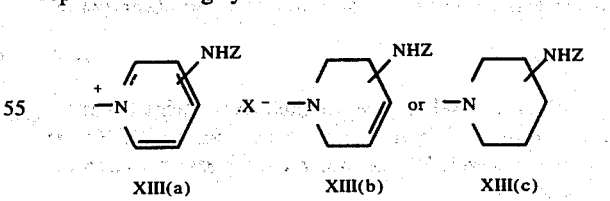

and Z is a protecting group known in the art for the protection of the amino function and A has the meanings defined immediately above), is subjected to hydrolysis, hydrogenolysis or some other reaction known in the art for the removal of the protecting group Z. As examples of Z, mention is made of those wherein Z is the group —COR and R is lower alkyl, lower alkyl and aryloxy (particularly methyl, ethoxy and phenoxy respectively) or aryl. Other examples of Z are benzyl, p-toluene-sulphonyl, phthalyl, trityl, trifluoroacetyl, formyl and benzylsulphonyl. Reference may be made to the review of protecting groups in Advances in Organic Chemistry, 3, 191–294 (Interscience Publishers 1963), and also to Chemistry of the Amino Acids by Greenstein and Winitz, Vol. 2, pages 885–924 (John Wiley & Sons, Inc., 1961). The compounds of general formula (XII) can be prepared following the information already given but using the appropriate acylating agent or other reagent to introduce the group Z.

A further aspect of the invention is the provision of a process for the preparation of compounds of formula (I) in which A is the —NH.CO.(CH$_2$)$_n$— group wherein $n$ is the integer 1, 2 or 3, in which process a reactive derivative (as herein before described) of an acid of formula

 (XIV)

is reacted with a primary amine of formula

[W]—NH$_2$ (XV)

[in which, $n$ is 1, 2 or 3,

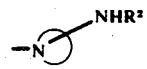

has the formula II($b$) or II($c$) and W and R$^2$ have the meanings defined in connection with formula (I)].

A still further aspect of the invention is the provision of a further process for the preparation of compounds of general formula (I) in which

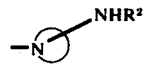

represents a ring system of formula II($b$) or II($c$), W and R$^1$ have the meanings defined in connection with formula (I), R$^2$ is the group —COR, R has the meanings defined in connection with formula (I) and A is a lower alkylene radical or the bivalent radical —NH.CO.(CH$_2$)$_n$— in which $n$ is 1, 2 or 3, and wherein the process consists of reacting a compound of the general formula

[W]—A—OH (XVI)

(in which W, and A have the meanings defined immediately above) with a compound of formula III($b$) or III($c$) (in which R$^2$ has the meaning defined immediately above).

The reaction is preferably carried out in the presence of a catalyst, for example Raney Nickel. An organic solvent, which is inert under the reaction conditions, is usually used for example xylene, toluene or benzene. Preferably the reaction is carried out by heating the reactants under reflux in a water-immiscible organic solvent, for example xylene, and removing the water formed during the reaction by azeotropic distillation. If necessary, reactive substituent groups can be blocked during a reaction and released later.

In order to prepare a compound of formula (I) in which

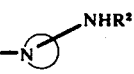

represents a ring system of formula II($b$) or II($c$), W has the meanings defined in connection with formula (I), R$^2$ is the —COR group wherein R has the meanings defined in connection with formula (I) and A is a mono-keto lower-alkylene radical of formula —CO.(CH$_2$)$_m$— in which $m$ is 1 to 5, a compound of formula

[W]—H (XVII)

can be acylated (Friedel-Crafts) with an acid halide of formula

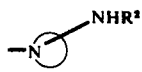 (XVIII)

For details of the reaction, reference may be made to "The Friedel-Crafts and related Reactions", G. A. Olah, Vol. 2 (Interscience Publishers, 1964).

The reactions outlined above usually are carried out in a solvent which is inert under the reaction conditions. The most suitable solvent system is chosen and varies depending on the particular reactants being employed. If necessary heating the reactants in solution under relfux can be carried out, and if necessary heating under high pressures may also be used.

Once a compound of general formula (I) has been prepared, then if necessary one or more substituents in the molecule may be converted to another substituent each within its own meanings specified in connection with formula (I). If a compound is produced in which

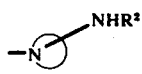

represents the pyridinium ring system of formula II($a$), this may be selectively reduced to one of the other ring systems of lower oxidation state. For example, reduction with an alkali metal borohydride gives the tetrahydropyridine ring system of formula II($b$). On the other hand, catalytic hydrogenation, for example, in the presence of Raney Nickel or a platinum catalyst, gives rise to the piperidine ring system of formula II($c$). Similarly, if a compound of formula (I) is prepared in which

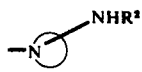

represents the tetrahydropyridine ring system of formula II($b$), this may also be reduced to the piperidine ring system of formula II($c$).

If a compound of formula (I) is prepared in which the chain A contains one or more carbonyl functions, then this chain may be selectively reduced. For example, when A is the oxalyl residue —CO.CO—, this may be reduced under mild conditions such as by a hydride transfer agent (particularly lithium aluminium hydride) to give the

residue. When A is the —CO—CH$_2$— residue this may be reduced with an alkali metal borohydride to give the

residue. When the oxalyl residue is reduced under more drastic conditions, the ethylene chain —CH$_2$—CH$_2$— results.

If a compound of formula (I) is produced in which R$^2$ is the —COR group, if necessary this may be hydrolysed to the compound of formula (I) in which R$^2$ is a hydrogen atom and which may then be reacted to give a compound of formula (I) in which R$^2$ is a different —COR group.

When a compound of formula (I) is produced wherein the radical W has one or more methoxy substituents, demethylation to the corresponding hydroxyl compound may be brought about in known manner. Furthermore, if the radical W has a nitro substituent this may be reduced in known manner to the corresponding amino compound which in turn may be further acylated or alkylated.

Compounds of formula I wherein W is Ar$_2$CHCH$_2$— may be prepared by catalytically hydrogenating a corresponding compound of formula I wherein W is Ar$_2$C:-CH—. The hydrogenation may be carried out with hydrogen in the presence of a hydrogenation catalyst such as a palladium or platinum catalyst. A suitable catalyst is palladium on carbon. If the compound of formula I has a pyridine ring of formula II(a) or a tetrahydropyridine ring of formula II(b) the hydrogenation can be carried out so as to reduce both the ethylenic bond and the ring system.

Compounds of formula I in which A contains a hydroxy group i.e. hydroxy-lower-alkylene or —O—CH$_2$CH(OH)CH$_2$, or wherein A is a branched chain alkylene radical posess an asymmetric carbon atom and are therefore capable of existing in optically active stereo isomeric forms. The optical isomers may be separated by standard resolution procedures. For instance compounds such as those which contain the ring system of formula II(b) or II(c) contain a basic nitrogen atom and may generally be resolved by treatment with a suitable optically active acid. Optically active acids are described in the literature and suitable ones for the resolution of any particular compound are chosed by experiment.

If necessary, in any of the reactions hereinbefore described, reactive substituent groups may be blocked during a reaction and released at a later stage. As already indicated the novel tetrahydropyridine and piperidine compounds provided by the invention contain a basic nitrogen atom and thus can form acid addition salts with acids (particularly pharmaceutically acceptable acids) or quaternary ammonium salts, for example with alkyl halides or aralkyl halides (particularly methyl iodide or benzyl chloride or bromide). The acid addition salts may either be formed in situ during the hereinbefore described processes and isolated therefrom or a free base may be treated with the appropriate acid in the presence of a suitable solvent and then the salt isolated. The quaternary salts may be prepared by treating the free base with the appropriate halide in the presence or absence of a solvent.

As already mentiond, the pharmaceutical compositions of the invention contain as active ingredients a compound of formula (I) as hereinbefore defined, which may be micronised. In addition to the active ingredient, said compositions also contain a non-toxic carrier. Any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10-80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other substances compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferably the pharmaceutical composition is in unit dosage form. In such form, the composition is subdivided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in package form. The quantity of active ingredient in a unit dose of composition may be varied or adjusted from 5 mg. or less to 500 or more, according to the particular need and the activity of the active ingredient. The invention also includes the compounds in the absence of carrier where the compounds are in unit dosage form.

The following non-limiting Examples illustrate the invention. Examples 2–4, 25, 28, 29, 72 and 73 illustrate the preparation of intermediates useful in preparing compounds to be used in the compositions and methods of the invention the remaining examples illustrate the preparation of compounds used in the invention.

EXAMPLE 1

1-[2-(cyclohexyl)ethyl]-4-benzamidopiperidine

2-Cyclohexylethyl bromide (1.9 g.) in dimethylformamide (10 ml.) was added to 4-benzamidopiperidine (2.2g.), diisopropylamine (4 ml.) and a trace of sodium iodide in dimethylformamide (10 ml). The mixture was heated at 70° C for 16 hours, cooled, poured into water, and extracted with methylene chloride. The washed and dried extracts were evaporated and the solid residue was recrystallised from ethanol to give the product (1.25 g.), m.p. 174°–5° C. (Found: C, 76.4; H, 9.5; N, 8.9 $C_{20}H_{30}N_2O$ requires C, 76.4; H, 9.6; N, 8.9%).

The product exhibits good hypotensive activity in standard test procedures.

EXAMPLE 2

1-[2-(3,4-Dimethoxyphenyl)ethyl]-4-acetamidopyridinium iodide 1-(2-Iodoethyl)-3,4-dimethoxybenzene (29.3 g.) and 4-acetamidopyridine (14.0 g.) in absolute ethanol (100 ml.) were refluxed for 2.5 hours. The resulting crystalline material was collectd and recrystallised from ethanol to give the title compound (29.1 g.), m.p. 201°–202° C. (Found: C, 47.9; H, 4.9; N, 6.3; $C_{17}H_{21}IN_2O_3$ requires C, 47.7; H, 4.9; N, 6.5%).

The product is an intermediate for the corresponding piperidine compound.

EXAMPLE 3

1-[2-(3,4-Dimethoxyphenyl)ethyl]-4-acetamidopiperidine

The quaternary salt of Example 2 (50 g.) and W7 Raney nickel (ca. 30 g.) in ethanol (600 ml.) containing triethylamine (13.1 g.) was hydrogenated at 700 p.s.i. and 80° C. for 4 hours. The filtrate, after removal of the catalyst was evaporated to dryness. Trituration of the residue with 2N sodium hydroxide solution caused crystallisation of 30.1 g. of the title compound, m.p. 152°–4° C. (Found: C, 66.4; H, 8.6; N, 9.1. $C_{17}H_{24}N_2O_3$ requires C, 66.6; H, 8.6; N, 9.1%).

The product exhibits depressant activity but is primarily useful as an intermediate for the corresponding 4-amino compound.

EXAMPLE 4

1-[2-(3,4-Dimethoxyphenyl)ethyl]-4-aminopiperidine

The acetamido compound of Example 3 (2.5 g.) in 2N hydrochloric acid (25 ml.) was heated under reflux for 3.5 hours. The cooled solution was basified and extracted with chloroform. Evaporation of the washed and dried extracts gave an oil which was treated with ethanolic hydrogen chloride to provide 1.67 g. of the title compound as its dihydrochloride, m.p. 260°–263° C. (Found: C, 53.4; H, 7.7; N, 8.3. $C_{15}H_{24}N_2O_2.2HCl$ requires C, 53.3; H, 7.8; N, 8.3%).

This compound exhibits hypotensive and depressant activity but is primarily useful as an intermediate for the corresponding 4-benzamido compound.

EXAMPLE 5

1-[2-(3,4-Dimethoxyphenyl)ethyl]-4-benzamidopiperidine

The amine dihydrochloride of Example 4 (2.0 g.) in methylene chloride (100 ml.) was stirred with potassium carbonate (2.76 g.) in water (50 ml.). Benzoyl chloride (1.8 ml.) in methylene chloride (20 ml.) was added slowly dropwise. Stirring was continued for 2 hours. The aqueous layer was separated and extracted with methylene chloride. Evaporation of the washed and dried methylene chloride layers gave an oil which was crystallised from ethanol to provide 1.80 g. of the title compound, m.p. 194°–195° C. (Found: C, 71.7; H, 7.7; N, 7.5. $C_{22}H_{28}N_2O_2$ requires C, 71.7; H, 7.7; N, 7.6%).

The product exhibits marked hypotensive activity.

EXAMPLE 6

1-[2-(3,4-Dimethoxyphenyl)ethyl]-4-(2-chlorobenzamido)-piperidine

The title compound as its hydrochloride (m.p. 250°–2° C) was prepared in the same way as for the compound of Example 5 but using o-chlorobenzoyl chloride in place of benzoyl chloride. (Found: C, 60.2; H, 6.1; N, 6.3. $C_{22}H_{26}Cl N_2O_3.HCl$ requires C, 60.3; H, 6.2; N, 6.4%).

The product exhibits hypotensive activity.

EXAMPLE 7

1-[2-(3,4-Dimethoxyphenyl)ethyl]-4-piperonylamidopiperidine

The title compound hydrochloride dihydrate (m.p. 285°–8° C) was prepared in the same way as for the compound of Example 5 but utilising piperonyloyl chloride in place of benzoyl chloride. (Found: C, 57.1; H, 6.8; N, 5.7. $C_{23}H_{28}N_2O_5.HCl.2H_2O$ requires C, 57.0; H, 6.8; N, 5.8%).

The product exhibits hypotensive and depressant activity.

EXAMPLE 8

1-[2-(3,4,5-Trimethoxyphenyl)ethyl]-4-benzamidopiperidine

Prepared in exactly the same way as for the compound of Example 1 except that 3,4,5-trimethoxyphenethyl chloride was used in place of cyclohexylethyl bromide. The title compound was obtained as a monohydrate (1.2 g.), m.p. 193°–4° C. (Found: C, 66.7; H, 7.6; N, 6.9. $C_{20}H_{30}N_2O_4.H_2O$ requires C, 66.4; H, 7.5; N, 6.7%).

The product exhibits hypotensive and depressant activity.

EXAMPLE 9

1-[2(3,4-Dihydroxyphenyl)ethyl]-4-benzamidopiperidine

4-Benzamido-1-[2-(3,4-dimethoxyphenyl)ethyl] piperidine (12.2 g.) in dry methylene chloride (400 ml.)

was added dropwise with stirring to a solution of boron tribromide (40 g.) in dry methylene chloride (120 ml.) at −50° C. The reaction mixture was kept at room temperature for 48 hours, then water was added with stirring. The resulting precipitate was collected and crystallised from ethanol. Recrystallisation from ethanol-ether gave the title compound as the hydrobromide, hemihydrate (6.0 g.), m.p. 256°–257° C. (Found: C, 56.1; H, 5.9; N, 6.4. $C_{20}H_{24}N_2O_3 \cdot HBr \cdot \frac{1}{2}H_2O$ requires C, 55.8; H, 6.1; N, 6.5%).

The product exhibits antihistamine and depressant activity but can also be used as an intermediate for the corresponding 3,4-dialkoxy compounds.

EXAMPLE 10

1-Phenacyl-4-benzamidopiperidine

Phenacyl bromide (2 g.), 4-benzamidopiperidine (2 g.) and potassium carbonate (2 g.) in isopropanol (25 ml.) were heated under reflux for 2 hours. The resulting solid was filtered, suspended in water and re-filtered to give the product (1.57 g.), m.p. 168° C (Found: C, 74.4; H, 6.8; N, 8.8. $C_{20}H_{22}N_2O_2$ requires C, 74.5; H, 6.9; N, 8.7%).

The product exhibits hypotensive and depressant activity.

EXAMPLE 11

1-[2-(3,4-Dihydroxyphenyl)-2-oxoethyl]-4-benzamidopiperidine

A mixture of 3,4-dihydroxyphenacyl chloride (18.65 g.), 4-benzamidopiperidine (20.40 g.) and potassium carbonate (20.7 g.) in isopropanol (400 ml.) was stirred under reflux for 2 hours, cooled, and filtered. The resulting solid was suspended in water, stirred for 30 minutes and filtered again to give the product as a quarter hydrate (11.24 g.) m.p. 219.5° C. (dec.) (Found: C, 66.8; H, 6.2; N, 7.5. $C_{20}H_{22}N_2O_4 \cdot \frac{1}{4}H_2O$ requires C, 66.9; H, 6.3; N, 7.8%). The product exhibits marked hypotensive activity.

EXAMPLE 12

1-[2-(1-Naphthyl)ethyl]-4-benzamidopiperidine 1-(2-Bromoethyl)naphthalene (3.0 g.) was added to a solution of 4-benzamidopiperidine (3.0 g.), di-isopropylamine (4 ml.) and a trace of sodium iodide in dimethylformamide (10 ml.). The mixture was heated at 70° C overnight, then poured into water and extracted with methylene chloride. The washed and dried extracts were evaporated and the residue was recrystallised from benzene to give the title compound (3.0 g.), m.p. 160°–162° C. (Found: C, 80.5; H, 7.4; N, 7.5 $C_{24}H_{26}N_2O$ requires C, 80.4; H, 7.3; N, 7.8%).

The product exhibits depressant activity.

EXAMPLE 13

1-[2-(2-Naphthyl)ethyl]-4-benzamidopiperidine

Prepared in a similar manner to the compound of Example 12 but using 2-(2-bromoethyl)-naphthalene in place of the 1-isomer. The product (m.p. 190°–3° C) was crystallised from isopropanol. (Found: C, 80.5; H, 7.5; N, 7.7. $C_{24}H_{26}N_2O$ requires C, 80.4; H, 7.3; N, 7.8%).

The product exhibits hypotensive activity. It also shows α-adrenoceptor antagonism, antihistamine and antiarrythmic activities.

EXAMPLE 14

1-[2-(3-Indenyl)ethyl]-4-benzamidopiperidine 3-(2-Bromoethyl)indene (1.12 g.), 4-benzamidopiperidine (1.02 g.) and potassium carbonate (1.38 g.) were heated under reflux in isopropanol (25 ml.) for 24 hours. The mixture was filtered and the filtrate was evaporated. Trituration of the residue with ether gave a solid which was recrystallised twice from aqueous ethanol to provide the title compound, m.p. 148°–149° C. (Found: C, 79.7; H, 7.6; N, 8.0. $C_{23}H_{26}N_2O$ requires C, 79.7; H, 7.6; N, 8.1%).

The product exhibits hypotensive activity and antihistamine activity.

EXAMPLE 15

1-[3-(3-Indenyl)propyl]-4-benzamidopiperidine

Prepared in a similar manner to the compound of Example 14 but using 3-(3-bromopropyl)indene in place of 3-(2-bromoethyl)indene. The title compound crystallised from isopropanol, m.p. 157°–9° C. (Found: C, 79.8; H, 8.1. N, 7.7. $C_{24}H_{28}N_2O$ requires C, 80.0; H, 7.8; N, 7.8%).

The product exhibits hypotensive and antihistamine activities.

EXAMPLE 16

1-[N-(2-Methylphenyl)carbamoylethyl]-4-benzamidopiperidine

A mixture of 3-chloropropion-o-toluidide (2.0 g.), 4-benzamidopiperidine (2.0 g.) and potassium carbonate (2.76 g.) in isopropanol (50 ml.) was stirred and heated under reflux for 18 hours. The hot mixture was filtered and the filtrate allowed to cool. The product (1.85 g., m.p. 195°–7° C) crystallised out. (Found: C, 72.6; H, 7.5; N, 11.5. $C_{22}H_{27}N_3O_2$ requires C, 72.3; H, 7.45; N, 11.5%).

The product exhibits depressant activity.

EXAMPLE 17

1-[1-(4-Acetamidophenoxy)-2-hydroxyprop-3-yl]-4-benzamidopiperidine

A solution of 2,3-epoxy-1-(4-acetamidophenoxy)-propane (5.18 g. and 4- benzamidopiperidine (6.13 g.) in isopropanol (250 ml.) was refluxed for 24 hours, cooled and a white crystalline solid was filtered off (8.90 g.). This was recrystallised from isopropanol to give 7.41 g. of the title compound as a quarter hydrate, m.p. 226°–8° C. (Found: C, 66.35; H, 7.1; N, 10.1. $C_{23}H_{29}N_3O_4 \cdot \frac{1}{4}H_2O$ requires C, 66.4; H, 7.15; N, 10.1%).

The product exhibits hypotensive activity and antihistamine activity.

EXAMPLE 18

1-(5-Acetamido-2-hydroxybenzyl)-4-benzamidopiperidine

4-Acetamidophenol (1.51 g.) and 39.4% aqueous formaldehyde (1.25 ml.) were dissolved in 50% aqueous ethanol, and 4-benzamidopiperidine (2.04 g.) was added. The resulting solution was heated under reflux for 30 minutes then left overnight at room temperature. The white solid was collected and purified by suspending in boiling ethanol and filtering to give the title compound (1.32 g.), m.p. 242° C. (Found: C, 68.15; H, 7.1;

N, 11.3. $C_{21}H_{25}N_3O_3$ requires C, 68.6; H, 6.9; N, 11.4%).

The product exhibits depressant activity.

EXAMPLE 19

1-[4-(4-Fluorophenyl)-4-oxobutyl]-4-benzamidopiperidine

4-Benzamidopiperidine (2.0 g.), 4'-chloro-p-fluorobutyrophenone (1.0 g.) and a trace of sodium iodide in dimethylformamide (5 ml.) were maintained at 70° C for 18 hours. On cooling, the solid which separated was collected, suspended in water, and refiltered. Recrystallisation from ethanol-water gave the title compound (0.52 g.), m.p. 161°–2° C. (Found: C, 71.9; H, 6.85; N, 7.5. $C_{22}H_{25}FN_2O_2$ requires C, 71.7; H, 6.8; N, 7.6%).

The product exhibits marked hypotensive activity and also α-adrenoceptor, antihistamine, depressant and antiinflammatory activity.

EXAMPLE 20

1-(2-Hydroxy-2-phenylethyl)-4-benzamidopiperidine

Sodium borohydride (6.00 g.) in 0.2N NaOH solution (60 ml.) was added dropwise to a stirred solution of 1-(2-phenyl-2-oxoethyl)-4-benzamidopiperidine (4.83 g.) in methanol (300 ml.). After refluxing the solution for 2 hours it was filtered and the filtrate concentrated to ca. 100 ml., whereupon the product crystallised out to give the title compound, m.p. 178°–180° C. (Found: C, 74.1; H, 7.5; N, 8.6. $C_{20}H_{24}N_2O_2$ requires C, 74.0; H, 7.5; N, 8.6%).

The product exhibits hypotensive activity and also antihistamine and antioxotremorine activity.

EXAMPLE 21

1-[3-(1-Naphthoxy)-2-hydroxyprop-1-yl]-4-benzamidopiperidine 3-(α-Naphthoxy)-1-chloropropan-2-ol (1.18 g.) was refluxed for 16 hours in isopropyl alcohol (100 ml.) with 4-benzamidopiperidine (1.032 g.) and anhydrous potassium carbonate (1.037 g.). The mixture was filtered hot, cooled and evaporated to dryness. The gum so obtained gave the title compound as a solid on triturating in ether, m.p. 139°–141° C. (Found: C, 74.1; H, 7.1; N, 6.9. $C_{25}H_{28}N_2O_3$ requires C, 74.2; H, 7.0; N, 6.9%).

The product exhibits hypotensive activity and also some depressant activity.

EXAMPLE 22

1-[2-(p-Nitrophenyl)ethyl]-4-benzamidopiperidine p-Nitrophenylethyl bromide (1.15 g.) was refluxed for 20 hours in isopropyl alcohol (75 ml.) with 4-benzamidopiperidine (1.032 g.) and anhydrous potassium carbonate (1.037 g.). The mixture was filtered hot, refrigerated and product was filtered off (547 mg.), washed with cold isopropyl alcohol and ether. The filtrate was evaporated to yield more product (1.4 g.). Recrystallisation from a mixture of benzene and petroleum ether (b.p. 40°–60° C) gave the title compound, m.p. 209°–216° C. (Found: C, 68.2; H, 6.7; N, 11.8. $C_{20}H_{23}N_3O_3$ requires C, 68.0; H, 6.6; N, 11.9%).

The product exhibits hypotensive activity and also depressant and anti-tremorine activities.

EXAMPLE 23

1-[2-(p-Aminophenyl)ethyl]-4-benzamidopiperidine

1-[2-(p-Nitrophenyl)ethyl]-4-benzamidopiperidine (3.0 g.) was hydrogenated in absolute alcohol (400 ml.) at 50 p.s.i. and 20° C for 3 hours in the presence of 300 mg. of platinum oxide as catalyst. The catalyst was filtered off and the solution evaporated to give the crude product as a foam. Crystallisation from a mixture of benzene and n-hexane gave the title compound, m.p. 193°–195° C. (Found: C,74.4; H, 7.9; N, 12.9. $C_{20}H_{25}N_3O$ requires C, 74.3; H, 7.8; N, 13.0%).

The product exhibits hypotensive activity and also depressant activity.

EXAMPLE 24

1-[2-(p-Acetamidophenyl)ethyl]-4-benzamidopiperidine

1-[2-(p-Aminophenyl)ethyl]-4-benzamidopiperidine (2.3 g.) was refluxed for 2 hours with acetic anhydride (22 ml.) in anhydrous pyridine (100 ml.). The solution was refrigerated for 24 hours and a crystalline product was filtered off, which after washing with ether yielded the title compound, m.p. 270°–275° C (dec.). Found: C, 72.6; N, 7.55; N, 11.6. $C_{22}H_{27}N_3O_2$ requires C, 72.3; H, 7.45; N, 11.5%).

The product exhibits hypotensive activity and also depressant and anti-tremorine activities.

EXAMPLE 25

1-[2-Phenethyl]-4-benzamidopyridinium bromide

A solution of 4-benzamidopyridine (7.92 g.) and 2-phenethyl bromide (9.25 g.) in absolute ethanol (100 ml.) was refluxed for 7.5 hours. Ether (100 ml.) was added and the mixture was allowed to stand overnight. The title compound (8.33 g.), m.p. 200°–203° C, was filtered off. (Found: C, 62.7; H, 5.0; N, 7.3. $C_{20}H_{19}BrN_2O$ requires C, 62.7; H, 5.0; N, 7.35%). The product is an intermediate for the corresponding piperidine compound.

EXAMPLE 26

1-Phenethyl-4-benzamido-1,2,5,6-tetrahydropyridine

4-Benzamido-1-phenethylpyridinium bromide (3.0 g.) in methanol (100 ml.) was treated with sodium borohydride (6.0 g.) in portions over 30 minutes. The solution was stirred during the addition and for 1 hour after. Water was then added to the warmed solution until crystallisation commenced to give the title compound (2.15 g.), m.p. 115°–7° C. (Found: C, 78.2; H, 7.3; N, 9.1. $C_{20}H_{22}N_2O$ requires C, 78.4; H, 7.2; N, 9.1%).

The product exhibits hypotensive activity.

EXAMPLE 27

1-Phenethyl-4-benzamidopiperidine a. A solution of 4-benzamidopyridine (7.92 g.) and 2-phenethyl bromide (9.25 g.) in absolute ethanol (100 ml.) was refluxed for 7.5 hours. Ether (100 ml.) was added and the mixture was allowed to stand overnight. 4-Benzamido-1-phenethylpyridinium bromide (8.33 g.), m.p. 200°–203° C was filtered off. (Found: C, 62.7; H, 5.0; N, 7.3. $C_{20}H_{19}BrN_2O$ requires C, 62.7; H, 5.0; N, 7.35%).

b. The quaternary salt (2.0 g.) in 95% ethanol (300 ml.) containing triethylamine (2.0 ml.) was hydrogenated in the presence of W7 Raney nickel catalyst (ca. 2 g.) at 400 p.s.i. and 85° C for 7 hours. The catalyst was filtered off and the filtrate was evaporated. Trituration of the residue with 2N sodium hydroxide solution gave a cream solid which was recrystallised from aqueous ethanol to provide the title compound (1.06 g.), m.p. 164°–166° C (Found: C, 77.8; H, 8.0; N, 9.2. Calculated for $C_{20}H_{24}N_2O$ C, 77.9; H, 7.8; N, 9.1%). Dissolution of the free base in ethanol and treatment with ethanolic hydrogen chloride followed by ether gave the hydrochloride of the title compound. Other salts are prepared from the free base in a similar manner.

The hydrochloride exhibits hypotensive activity.

EXAMPLE 28

1-Phenethyl-4-acetamidopiperidine.

a. A solution of phenethyl bromide and 4-acetamidopyridine in absolute ethanol was heated under reflux, cooled, treated with ether and allowed to stand overnight to give 1-phenethyl-4-acetamidopyridinium bromide.

b. The above quaternary salt in ethanol containing triethylamine and W7 Raney nickel was hydrogenated at 400 p.s.i. and 80° C. The catalyst was then filtered off and the filtrate evaporated to dryness to give a residue which on triturating with 2N sodium hydroxide solution gave the title compound.

Dissolution of the free base in ethanol followed by treatment with ethanolic hydrogen chloride and ether gave the hydrochloride of the title compound.

EXAMPLE 29

1-Phenethyl-4-phenylacetamidopiperidine a. The acetamido compound of Example 28 in 2N hydrochloric acid was heated under reflux for 3.5 hours, cooled, basified and extracted with chloroform. Evaporation of the washed and dried extracts gave a residue which on treating with ethanolic hydrogen chloride gave the corresponding acid addition salt of 1-phenethyl-4-amino-piperidine.

b. The above amino compound was treated with phenacyl chloride in a mixture of methylene chloride and water containing potassium carbonate to give the title compound. Acid addition salts were prepared in a similar manner to that described in Example 27.

EXAMPLE 30

1-Benzyl-4-benzamidopiperidine

1-Benzyl-4-piperidone was converted into the corresponding oxime derivative which on reduction gave 1-benzyl-4-aminopiperidine. Treatment of the amino compound with benzoyl chloride in a mixture of methylene chloride and water containing potassium carbonate afforded the title compound from which salts can be prepared in a similar manner to that described in Example 27.

EXAMPLE 31

1-Benzyl-4-(p-chlorobenzamido)piperidine.

The 1-benzyl-4-aminopiperidine prepared in Example 30 was treated with p-chlorobenzoyl chloride in a similar manner to that described in the same example and the product converted to a salt.

EXAMPLE 32

1-Benzyl-4-(p-methylbenzamido)piperidine.

The 1-benzyl-4-aminopiperidine prepared in Example 30 was treated with p-methylbenzoyl chloride in a similar manner to that described in the same example and the product converted to a salt.

EXAMPLE 33

1-[2-(o-Nitrophenyl)ethyl]-4-benzamido-piperidine

A mixture of 2-(o-nitrophenyl)ethyl bromide (1.15 g.), 4-benzamidopiperidine (1.02 g.) and potassium carbonate (1.04 g.) in isopropanol (75 ml.) was stirred and refluxed for 24 hours. The hot mixture was filtered, the filtrate evaporated and the residue crystallised from ethanolic hydrogen chloride and ether to give the title compound as the hydrochloride, (47 mg.), m.p. 236°–241° C. (Found: C, 61.31; H, 6.1; N, 10.6. $C_{20}H_{23}N_3O_3.HCl$ requires C, 61.6; H, 6.2; N, 10.8%).

The product exhibits hypotensive activity.

EXAMPLE 34

1-[3,4-Dichlorobenzoyl)methyl]-4-benzamidopiperidine

A mixture of 3,4-dichlorophenyl chloromethyl ketone (2.24 g.), 4-benzamidopiperidine (2.04 g.) and triethylamine (1.11 g.) was stirred in dry dimethylformamide (60 ml.) at room temperature for 18 hours. The solution was evaporated and the residue was crystallised from ethanolic hydrogen chloride and ether to give the title compound as the hydrochloride (1.45 g.), m.p. 226° C. (Found: C, 56.3; H, 5.3; N, 6.8. $C_{20}H_{22}Cl_2N_2O_2.HCl$ requires H, 56.15; H, 4.95; N, 6.55%).

The product exhibits hypotensive and depressant activities.

EXAMPLE 35

1-[2-(o-Aminophenyl)ethyl]-4-benzamidopiperidine

A solution of 1-[2-(o-nitrophenyl)ethyl]-4-benzamidopiperidine (4.25 g.) in absolute ethanol (150 ml.) was added over 50 minutes to stirred stannous chloride (10.82 g.) in concentrated hydrochloric acid (12 ml.) and water (7.5 ml.) at 60°–70° C. After addition, the mixture was stirred at this temperature for 4 hours before cooling and evaporating the ethanol. Continuous extraction into chloroform of the neutralised (with 2N sodium hydroxide solution) aqueous fraction gave the title compound (1.65 g.). The aqueous layer after extraction was made alkaline with 2N sodium hydroxide solution and extracted with more chloroform to give a further batch of the title compound (2.36 g.). The total product was crystallised from ethanolic hydrogen chloride and ether to give the hydrochloride of the title compound (2.75 g.), m.p. 263.8° C. (Found: C, 60.3; H, 7.0; N, 10.5. $C_{20}H_{25}N_3O.2HCl$ requires C, 60.6; H, 6.9; N, 10.60%).

The product exhibits hypotensive and depressant activities.

EXAMPLE 36

1-[2-(3,4-Dichlorophenyl)-2-hydroxyethyl]-4-benzamidopiperidine

Sodium borohydride (15.0 g.) in 0.2N sodium hydroxide solution (200 ml.) was added over 30 minutes to a stirred solution of 1-[3,4-dichlorobenzoyl)methyl]-4-benzamidopiperidine monohydrochloride (6.45 g.) in methanol (260 ml.). Stirring was continued for 3 days after the addition, and the mixture was then refluxed for 2 hours. The precipitated product was filtered from the hot mixture, washed with cold water and dried to give 4.83 g. of the title compound. This was crystallised from ethanolic hydrogen chloride and ether to give the hydrochloride (4.86 g.) m.p. 270.0° C. (Found: C, 55.8; H, 5.5; N, 6.4. $C_{20}H_{22}Cl_2N_2O_2$.HCl requires C, 55.9; H, 5.4; N, 6.5%).

The product exhibits hypotensive and anti-convulsant activities.

EXAMPLE 37

1-[2-(3,4-Dichlorophenyl)ethyl]-4-benzamidopiperidine

4-Benzamidopiperidine (204 mg.) and anhydrous potassium carbonate (138 mg.) were intimately ground together and added to 2-(3,4-dichlorophenyl)ethyl bromide (254 mg.). The resulting paste was heated at 100° C for 2 hours to give a hard solid. This was broken up, washed well with water and ether and dried to give the title compound (355 mg.). Recrystallisation from ethanolic hydrogen chloride and ether gave the hydrochloride (237 mg.), m.p. 286.0° C. (Found: C, 58.2; H, 5.8; N, 6.8. $C_{20}H_{22}Cl_2N_2O$.HCl requires C, 58.05; H, 5.6; N, 6.8%).

The product exhibits good hypotensive activity. It also possesses α-adrenoceptor antagonism, antihistamine and anti-tremorine activities.

EXAMPLE 38

1-[2-(2,6-Dichlorophenyl)ethyl]-4-benzamidopiperidine.

2-(2,6-Dichlorophenyl)ethyl bromide (674 mg.) was reacted with 4-benzamidopiperidine (547 mg.) in the presence of anhydrous potassium carbonate (736 mg.) following the procedure of Example 37 to give the title compound as the hydrochloride (412 mg) m.p. 285.7° C after crystallisation from ethanolic hydrogen chloride and ether. (Found: C, 58.0; H, 5.6; N, 6.7. $C_{20}H_{22}Cl_2N_2O$.HCl requires C, 58.05; H, 5.6; N, 6.8%).

The product exhibits hypotensive activity, also anti-tremorine and depressant activities.

EXAMPLE 39

1-[3-Phenylpropyl]-4-benzamidopiperidine

3-Phenylpropyl bromide (2.7 g.) was reacted with 4-benzamidopiperidine (3.39 g.) in the presence of anhydrous potassium carbonate (2.28 g.) following the procedure of Example 37 to give the title compound as the hydrochloride, quarter hydrate (1.96 g.), m.p. 237.2° C after crystallisation from ethanolic hydrogen chloride and ether. (Found: C, 69.6; H, 7.6; N, 7.6. $C_{21}H_{26}N_2O$.HCl.¼ $H_2O$ requires, C, 69.4; H, 7.6; N, 7.7%).

The product exhibits good hypotensive activity and also α-adrenoceptor antagonism, anti-histamine and anti-tremorine activities.

EXAMPLE 40

1-[4-(p-Fluorophenyl)-n-butyl]-4-benzamidopiperidine

Hydrazine hydrate (80%, 60 ml.) was added to 1-[4-(p-fluorophenyl)-4-oxobutyl]-4-benzamidopiperidine (11.08 g.) dissolved in warm ethylene glycol (125 ml.) and the solution was refluxed gently for 60 minutes (135°-140° C). Potassium hydroxide pellets were added (6.0 g.) and excess water and hydrazine were distilled off until the temperature rose to 185° C. Refluxing was continued for 30 minutes at this temperature and the hot solution was poured into cold water (500 ml.). the precipitated product was filtered off and after two crystallisations from ethanolic hydrogen chloride and ether the hydrochloride, hemihydrate of the title compound was obtained (1.85 g.) m.p. 228.3° C. (Found: C, 66.1; H, 7.4; N, 7.4. $C_{22}H_{27}FN_2O$.HCl.½$H_2O$ requires C, 66.1; H, 7.3; N, 7.0%).

The product exhibits hypotensive activity and also α-adrenoceptor antagonism and anti-histamine activity.

EXAMPLE 41

1-[2-(3,4-Dimethylphenyl)ethyl]-4-benzamidopiperidine 2-(3,4-Dimethylphenyl)ethyl bromide (4.57 g.) was combined with 4-benzamidopiperidine (4.09 g.) in the presence of anhydrous potassium carbonate (2.76 g.) following the procedure of Example 37 to give the hydrochloride, hydrate of the title compound (3.07 g.), m.p. 276.0° C. (Found: C, 67.9; H, 7.7; N, 7.1. $C_{22}H_{28}N_2O$.HCl.$H_2O$ requires C, 67.6; H, 8.0; N, 7.2%).

The product exhibits hypotensive activity.

EXAMPLE 42

4-benzamido-1-[4-(p-fluorophenyl)-4-oxobutyl]-piperidine

4-Chloro-4¹-fluorobutyrophenone (5.5 g.) was reacted with 4-benzamidopiperidine (5.1 g.) in the presence of anhydrous potassium carbonate (3.45 g.) following the procedure of Example 37 to give the title compound as the hydrochloride (4.84 g.), m.p. 257.9° C from ethanolic hydrogen chloride and ether. (Found: C, 65.1; H, 6.5; N, 6.7 $C_{22}H_{25}FN_2O_2$.HCl requires C, 65.25; H, 6.2; N, 6.9%).

The product displayed marked hypotensive activity and also was shown to possess α-adrenoceptor antagonist, antihistamine and anti-inflammatory activity.

EXAMPLE 43

4-Benzamido-1-(4-phenyl-4-oxobutyl)piperidine

γ-Chlorobutyrophenone (3.64 g.) was reacted with 4-benzamidopiperidine (4.08 g.) in the presence of anhydrous potassium carbonate (2.76 g.) following the procedure of Example 37 to give the title compound as the hydrochloride quarter hydrate (3.89 g.), m.p. 241.1° C from ethanolic hydrogen chloride and ether. (Found: C, 67.9; H, 7.1; N, 7.1. $C_{22}H_{26}N_2O_2$.HCl.¼ $H_2O$ requires C, 67.5; H, 7.1; N, 7.2%).

The product exhibited marked hypotensive activity and also was shown to possess α-adrenoceptor antagonist, antihistamine and antiarrythmic activities.

EXAMPLE 44

4-benzamido-1-[4-(2,5-dimethylphenyl)-4-oxobutyl]-piperidine

4-Chloro-2,5-dimethylbutyrophenone (1.05 g.) was reacted with 4-benzamidopiperidine (1.02 g.) in the presence of anhydrous potassium carbonate (0.69 g.) following the procedure of Example 37 to give the title compound as the hydrochloride (0.80 g.), m.p. 190.0° C from ethanolic hydrogen chloride and ether. (Found: C, 69.45; H, 7.7; N, 6.55. $C_{24}H_{30}N_2O_2 \cdot HCl$ requires C, 69.5; H, 7.5; N, 6.75%).

The product displayed hypotensive activity and also antihistamine and α-adrenoceptor antagonist activities.

EXAMPLE 45

4-Benzamido-1-[4-(2,4-dimethylphenyl)-4-oxo-butyl]-piperidine

4-Chloro-2,4-dimethylphenylbutyrophenone (4.20 g.) was reacted with 4-benzamidopiperidine (4.08 g.) in the presence of anhydrous potassium carbonate (2.76 g.) following the procedure of Example 37 to give the title compound as the hydrochloride (2.92 g.), m.p. 215.2° C from ethanolic hydrogen chloride and ether. (Found: C, 69.1; H, 7.6; N, 6.5. $C_{24}H_{30}N_2O_2 \cdot HCl$ requires C, 69.5; H, 7.5; N, 6.75%).

The product exhibited hypotensive activity and also antihistamine and α-adrenoceptor antagonist activity.

EXAMPLE 46

1-(4-Phenylbutyl)-4-benzamidopiperidine

1-Bromo-4-phenylbutane (6.39 g.) and 4-benzamidopiperidine (6.12 g.) were reacted in the presence of anhydrous potassium carbonate (4.14 g.) following the procedure of Example 37 to give the title compound as the hydrochloride quarter hydrate (8.10 g.), m.p. 240.7° C from ethanolic hydrogen chloride and ether. (Found: C, 69.8; H, 7.9; N, 7.2. $C_{22}H_{28}N_2O \cdot HCl \cdot \frac{1}{4} H_2O$ requires C, 70.0; H, 7.9; N, 7.4%).

The product exhibited hypotensive activity and also α-adrenoceptor antagonist and antihistamine activity.

EXAMPLE 47

4-Benzamido-1-(3,4-methylenedioxybenzyl)piperidine 3,4-Methylenedioxybenzyl chloride (5.76 g.), 4-benzamido-piperidine (6.89 g.) and anhydrous potassium carbonate (7.00 g.) were stirred at room temperature for 5 hours in isopropanol (50 ml.). Additional isopropanol (100 ml.) was added and stirring continued for 3 hours. The mixture was then heated to the boiling point and filtered whilst hot. Filtration provided the title compound as the hemi-hydrate (7.94 g.), m.p. 179.5°-180.5° C. A second crop (1.23 g.) was obtained on concentration of the mother liquors. (Found: C, 69.2; H, 6.55; N, 8.2. $C_{20}H_{22}N_2O_3 \cdot \frac{1}{2}H_2O$ requires C, 69.15; H, 6.7; N, 8.1%).

The product exhibited hypotensive activity and also anti-inflammatory activity.

EXAMPLE 48 cl

4-Benzamido-1-[2-(p-chlorophenyl)ethyl]piperidine 2-(p-Chlorophenyl)ethanol p-toluenesulphonate ester (9.8 g.), 4-benzamidopiperidine (6.49 g.) and anhydrous potassium carbonate (8.78 g.) were refluxed in isopropanol (150 ml.) for 12 hours and the mixture filtered hot. On cooling, the filtrate deposited the title compound as colourless crystals, (5.4 g.), m.p. 190°-195° C. (Found: C, 70.3; H, 6.9; N, 8.1. $C_{20}H_{23}ClN_2O$ requires C, 70.1; H, 6.8; N, 8.2%).

The product exhibited hypotensive activity and also anti-convulsant activity.

EXAMPLE 49

4-Benzamido-1-[2-(p-methoxyphenyl)ethyl]piperidine 2-(p-Methoxyphenyl)ethanol p-toluenesulphonate ester (1.53 g.), 4-benzamidopiperidine (1.02 g.) and anhydrous potassium carbonate (1.10 g.) were refluxed in isopropanol (50 ml.) for 8 hours and the mixture worked up as in Example 48 to provide the title compound, which was further recrystallized from ethyl acetate as colourless needles (0.78 g.), m.p. 178° C. (Found: C, 74.7; H, 7.9; N, 8.45. $C_{21}H_{26}N_2O_2$ requires C, 74.5; H, 7.7; N, 8.3%).

The product was shown to possess hypotensive activity.

EXAMPLE 50

N-Phenyl-4-(p-benzamidopiperid-1-yl)butyramide

4-Benzamido-1-(3-methoxycarbonyl)propylpiperidine (5 g.) was refluxed in redistilled aniline (25 ml.) under nitrogen for 18 hours. Filtration of the cooled mixture afforded the title compound which provided a colourless crystalline hydrochloride hemihydrate from ethanolic hydrogen chloride and ether, (4.5 g.), m.p. 203° C (Found: C, 64.4; H, 6.95; N, 10.2. $C_{22}H_{27}N_3O_2 \cdot HCl \cdot \frac{1}{2}H_2O$ requires C, 64.3; H, 7.1; N, 10.2%).

The product exhibited hypotensive activity.

EXAMPLE 51

4-Benzamido-1-[4-(p-chlorophenyl)-4-oxobutyl]-piperidine

4-Chloro-4'-chlorobutyrophenone (2.17 g.) was added to a well-ground mixtue of 4-benzamidopiperidine (2.04 g.) and anhydrous potassium carbonate (1.38 g.) and the mixture heated to 100° C for 1 hour. The solid residue was slurried with hot water (100 ml.) for 3 hours, filtered, washed with ether and dried to give a cream coloured solid. This solid was dissolved in ethanolic hydrogen chloride, treated with ether and then cooled to 0° to give the title compound as its hydrochloride (1.9 g.) m.p. 242°-243° C. (Found: C, 62.8; H, 6.2; N, 6.55. $C_{22}H_{25}ClN_2O_2 \cdot HCl$ requires C, 62.7; H, 6.0; N, 6.65%).

The product possessed hypotensive activity. It also exhibited highly potent α-adrenoceptor antagonist activity. Further this compound was shown to possess anti-histamine and anti-inflammatory activity.

EXAMPLE 52

1-(2-Phenoxyethyl)-4-benzamidopiperidine

2-Phenoxyethylbromide (2.01 g.), 4-benzamidopiperidine (2.04 g.) and anhydrous potassium carbonate (1.38 g.) were reacted together according to the procedure of Example 51. The title compound as its hydrochloride (2.06 g.) had m.p. 207° C. (Found: C, 67.0; H, 7.1; N, 7.7. $C_{20}H_{24}N_2O_2 \cdot HCl$ requires C, 67.3; H, 7.1; N, 7.85%).

The product possessed marked hypotensive activity.

EXAMPLE 53

4-Benzamido-1-(4-phenyl-4-hydroxybutyl)piperidine

4-Benzamido-(4-phenyl-4-oxobutyl)piperidine (3.4 g.) was dissolved in methanol (125 ml.) and a solution of sodium borohydride (6.0 g.) in 0.2N sodium hydroxide (30 ml.) was added at room temperature over a period of 0.5 hours. The resulting mixture was stirred for a further 2 hours and then heated under reflux for 4 hours. The resulting mixture was filtered, the filtrate evaporated almost to dryness and then treated with water (100 ml.). The colourless solid was filtered off, washed with water, dried, dissolved in a small amount of ethanolic hydrogen chloride and treated with ether until crystallisation commenced. Filtration and drying gave 1.875 g. of the hydrochloride of the title compound, m.p. 221° C. (Found: C, 68.1; H, 7.4; N, 7.3. $C_{22}H_{28}N_2O_2.HCl$ requires C, 67.9; H, 7.5; N, 7.2%).

The product exhibited hypotensive activity.

EXAMPLE 54

1-[4-(p-Fluorophenyl)-4-hydroxybutyl]-4-benzamidopiperidine

4-Benzamido-1-[4-(p-fluorophenyl)-4-oxobutyl]-piperidine (7.4 g.) in methanol (100 ml.) was treated during 25 minutes at room temperature with a solution of sodium borohydride (20 g.) in 0.2N sodium hydroxide (200 ml.). The resulting mixtures was then worked up as in Example 53 to give the title compound as its hydrochloride, m.p. 241° C (decomp.). (Found: C, 65.35; H, 7.0; N, 6.9. $C_{22}H_{27}F\ N_2O_2.HCl$ requires C, 64.9; H, 6.9; N, 6.9%).

The product exhibited hypotensive activity and also possessed potent antihistamine activity.

EXAMPLE 55

1-[3-(1-Naphthyloxy)-propyl]-4-benzamidopiperidine

The title compound as its hydrochloride, m.p. 228° C (decomp.), was prepared by the method of Example 52 using 3-naphthyloxypropyl bromide (2.07 g.), 4-benzamidopiperidine (1.8 g.) and anhydrous potassium carbonate (1.24 g.). (Found: C, 70.4; H, 7.0; N, 6.6. $C_{25}H_{28}N_2O_2\ HCl$ requires C, 70.65; H, 6.9; N, 6.6%).

The product exhibited marked hypotensive activity.

EXAMPLE 56

1-[2-(1,2,3,4-Tetrahydro-6-napthyl)-2-oxoethyl]-4-benzamidopiperidine

A solution of 6-chloroacetyl-1,2,3,4-tetrahydro napthalene (20.87 g.), 4-benzamidopiperidine (20.4 g.) and trimethylamine (11.1 g.) in dimethylformamide (200 ml.). was stirred for 3 days at room temperature. The crystals which had formed during this time were then filtered off, washed and dried. A portion of this crystalline solid (4.0 g.) was dissolved in ethanol (50 ml.) and acidified with ethanol hydrogen chloride to give 4.0 g. of the hydrochloride of the title compound, m.p. 270° C (decomp.). (Found: C, 69.5; H, 7.2; N, 6.8; $C_{24}H_{28}N_2O_2.HCl$ requires C, 69.8; H, 7.1; N, 6.8%).

The product exhibited hypotensive activity.

EXAMPLE 57

1-[2-(1,2,3,4-Tetrahydro-6-napthyl)-2-hydroxyethyl]-4-benzamido-piperidine

The title compound as its hydrochloride, m.p. 253° C (decomp.), was prepared by reduction of the free base of the compound obtained in Example 56 using sodium borohydride. The procedure is that described in Example 53. (Found: C, 69.7; H, 7.5; N, 6.6. $C_{24}H_{30}N_2O_2.HCl$ requires C, 69.5; H, 7.5; N, 6.75%).

The product exhibited hypotensive activity.

EXAMPLE 58

1-[4-(1,2,3,4-Tetrahydro-6-naphthyl)-4-oxobutyl]-4-benzamidopiperidine

6-Chlorobutyryl-1,2,3,4-tetrahydronaphthalene (6.4 g.), 4-benzamidopiperidine (2.0 g.) and anhydrous potassium carbonate (1.38 g.) were reacted and worked up as described in Example 51 to give the hydrochloride of the title compound, m.p. 221° C. (Found: C, 68.4; H, 7.7; N, 6.0. $C_{26}H_{32}N_2O_2.HCl.H_2O$ requires C, 68.0; H, 7.7; N, 6.1%.

The product exhibited hypotensive activity.

EXAMPLE 59

1-Phenethyl-4-benzamidopiperidine hydrochloride

The free base of Example 27 (7.4 g.) was dissolved in boiling ethanol (100 ml.), the solution filtered and the filtrate made acid by addition of ethanolic hydrogen chloride. On cooling, 7.0 g. of the quarter hydrate of the title compound were obtained, m.p. 281° C (decomp). (Found: C, 68.55; H, 7.5; N, 7.9. $C_{20}H_{24}N_2O.HCl\ \frac{1}{4}H_2O$ requires C, 68.6; H, 7.6; N, 8.0%).

The product exhibited hypotensive activity.

EXAMPLE 60

4-Benzamido-1-phenethylpiperidine

2-Phenylethanol (0.61 g., 0.005 mole), 4-benzamidopiperidine (1.02 g., 0.005 mole) and Raney Nickel (W7, ca. 2g.) were stirred in xylene (50 ml.) and the mixture boiled under reflux for 16 hours. Liberated water was removed by means of a Dean and Stark apparatus. Filtration of the hot mixture provided a yellow solution which was stored at room temperature until crystallisation was complete. The title compound was obtained as cream needles (0.85 g.), m.p. 164°–7° C.

The product exhibited hypotensive activity.

EXAMPLE 61

4-Benzamido-1-[2-(2-naphthyl)ethyl]piperidine 2-(2-Naphthyl)ethanol (3.44 g., 0.02 mole), 4-benzamidopiperidine (4.08 g., 0.02 mole) and Raney Nickel (W7 ca. 5 g.) were suspended in xylene (200 ml.) and the stirred mixture boiled under reflux for 16 hours. Liberated water was removed by means of a Dean and Stark apparatus. The mixture was filtered hot and evaporated to ca. 100 ml. The resulting yellow solution was stored until crystallisation was complete. The title compound was obtained as off-white needles (3.30 g.), m.p. 189°–191° C.

The product exhibited hypotensive activity.

EXAMPLE 62

The following compounds were prepared in a similar manner to that described in the hereinbefore disclosed Examples and processes:

1-(2-Phenylprop-1-yl)-4-benzamidopiperidine.
1-(2-Phenylbut-1-yl)-4-benzamidopiperidine.
1-(3-Phenylprop-2-yl)-4-benzamidopiperidine.
1-(4-Phenylbut-3-yl)-4-benzamidopiperidine.
1-(3-Phenylbut-2-yl)-4-benzamidopiperidine.
1-[4-(Quinol-2-yl)buty-1-yl]-4-benzamidopiperidine.
1-[5-(Quinol-2-yl)pent-1-yl]-4-benzamidopiperidine.
1-[6-(Quinol-2-yl)hex-1-yl]-4-benzamidopiperidine.
1-[2(Quinol-2-yl)eth-1-yl]-4-benzamidopiperidine.
1-[3(Quinol-2-yl)prop-1-yl]-4-benzamidopiperidine.

1-[4(Quinol-2-yl)but-1-yl]-4-benzamidopiperidine.
1-(3-Cyclohexylbut-1-yl)-4-benzamidopiperidine.
1-[2-Cyclohexylmethylprop-1-yl]-4-benzamidopiperidine.
1-[4-Cyclohexylbut-2-yl]-4-benzamidopiperidine.
1-[2-(o-Chlorophenyl)ethyl]-4-benzamidopiperidine.
1-[2-(o-and p-Methylphenyl)ethyl]-4-benzamidopiperidine.
1-[2-(o-and p-Ethylphenyl)ethyl]-4-benzamidopiperidine.
1-[2-(o-and p-Propylphenyl)ethyl]-4-benzamidopiperidine.
1-[2-(o-and p-Butylphenyl)ethyl]-4-benzamidopiperidine.
1-[2-(p-Dimethylaminophenyl)ethyl]-4-benzamidopiperidine.
1-[2-(p-Diethylaminophenyl)ethyl]-4-benzamidopiperidine.
1-[2-(p-Ethoxycarbonylphenyl)ethyl]-4-benzamidopiperidine.
1-[2-(p-Carboxyphenyl)ethyl]-4-benzamidopiperidine.
1-Benzyl-4-acetamidopiperidine.
1-(2,6-Dichlorophenylmethyl)-4-benzamidopiperidine.
1-(2,6-Dichlorophenylethyl)-4-benzamidopiperidine.
1-[2-(2-Naphthyloxy)ethyl]-4-benzamidopiperidine.
1-[3-(2-Naphthyloxy)propyl]-4-benzamidopiperidine.
1-[2-(m-Trifluoromethylphenyl)ethyl]-4-benzamidopiperidine.
1-[2-(p-biphenylyl)ethyl]-4-benzamidopiperidine.
1-[2-(3,4-Methylenedioxyphenyl)ethyl]-4-benzamidopiperidine.
1-(2-Cyclopentylethyl)-4-benzamidopiperidine.
1-(2-Cycloheptylethyl)-4-benzamidopiperidine.
1-[2-(7-Carbethoxymethoxy-4-methyl-2-oxo-chromen-3-yl)ethyl]-4-benzamidopiperidine.

EXAMPLE 63

4-Benzamido-1-[4-(4-hydroxyphenyl)-4-oxobutyl]-piperidine p-(4-Chlorobutyl)phenol (130 g 4-benzamidopiperidine (134 g ) triethylamine (70 g.) and dimethylformamide were stirred at 60° C for 2 days allowed to stand overnight then filtered. The filtrate was diluted with a large volume of diethylether whereupon an oil precipitated which crystallised after being allowed to stand. This precipitate was filtered off, washed with diethylether then water, dried and converted to the hydrochloride using hydrogen chloride gas dissolved in a mixture of isopropyl alcohol and ethanol to afford 4-benzamido-1-[4-(4-hydroxyphenyl)-4-oxobutyl] piperidine hydrochloride (43.5 g. 16%) m.p. 276° C. Analysis: Found: C, 65.60; H, 6.73; N, 6.75% $C_{22}H_{26}N_2O_3HCl$ requires C, 65.80; H, 6.78; N, 6.97%.

The product has good hypotensive activity and remarkably low toxicity namely an $LD_{50}$ in the mouse: Orally: 24 hour, 7 and 14 days, > 4000 mg/kg. i.p. 24 hour, > 4000 mg/kg. 7 and 14 days 1630 mg/kg.

It also exhibited α-adrenoceptor antagonism.

EXAMPLE 64

1-[1-Methyl-2-(4-hydroxy)phenyl-2-oxoethyl]-4-benzamidopiperidine

4-Benzamidopiperidine (4.086 g. and p-hydroxy-α-bromopropiophenone (6.160 g.) were heated together at 100° for 2 hours in the presence of finely-grounded anhydrous potassium carbonate (2.764 g., To the solid residue was added water (200 ml.) and the product was extracted into ether. The dried ($MgSO_4$) extract was evaporated down to give the title compound as the crude base. This base was dissolved in a minimum quantity of hot ethanol to which ethanolic HCl was added until just acid. Ethyl acetate was added to give a slight turbidity and on cooling the product crystallised out as the hydrochloride heimhydrate (4.725 g., 60%,) m.p. 224.1° (dec). Calculated for $C_{21}H_{24}N_2O_3.HCl.½λ H_2O$ C: 63.37; H, 6.59; N, 7.04. Found: C, 63.32; H, 6.36; N, 6.79.

The product can be used as an intermediate in the preparation of the compound of the next example.

EXAMPLE 65

1-[1-Methyl-2-(4-hydroxy)phenyl-2-hydroxyethyl]-4-benzamidopiperidine.

1-[1-Methyl-2-(4-hydroxy)phenyl-2-oxoethyl]-4-benzamidopiperidine (3.524 g., 0.01 mole) was dissolved in methanol (80 ml.) at room temperature. To the stirred solution was added slowly sodium borohydride (10 g.) in sodium hydroxide solution (200 ml., 0.2 N). The mixture was stirred overnight, then refluxed for two hours and the methanol boiled off before cooling the reaction mixture. The product was extracted into chloroform. The dried ($MgSO_4$) extract was evaporated to give a white foam (2.441 g.). The title compound was crystallised as the bae from $MeOH/H_2O$ and then converted to its hydrochloride (m.p. >130° (dec.) by treatment with HCl in ethanol. Calculated for $C_{21}H_{26}N_2O_3.HCl.¾H_2O$. C: 62.36; H: 7.11; N, 6.93. Found: C: 62.37; H, 6.99; N, 6.51%.

The product exhibited hypotensive activity in a standard test procedure.

EXAMPLE 66

A. 1,1,3,4,4,6-Hexamethyl-7-bromoacetyl-1,2,3,4-Tetrahydronaphthalene.

A solution of 1,1,3,4,4,6-Hexamethyl-7-acetyl-1,2,3,4-tetrahydronaphthalene (33 g.) in 40 ml. glacial acetic acid was treated slowly with 20 g. bromine. Warming was necessary to initiate the reaction, evidenced by disappearance of the red colouration. When all the bromine had been added, the mixture was cooled and poured onto ice to give a pale green gum. The whole was extracted with ether, the ethereal extracts washed with dilute $Na_2CO_3$, water and finally dried over $MgSO_4$. Evaporation of the ether gave a pale green solid which was recrystallised from EtOH to give the title compound 27.6 g. (64%), m.p. 68° C. Analysis : Calculated for $C_{18}H_{25}OBr$, C, 64.09%; H, 7.47%. Found : C, 64.40%; H, 7.65%.

B. 7-(4-Benzamidopiperidinoacetyl)-1,1,3,4,4,6-hexamethyl-1,2,3,4-tetrahydronaphthalene A mixture of 1,1,3,4,4,6-hexamethyl-7-bromoacetyl-1,2,3,4-tetrahydronaphthalene (7 g.), 4-benzamidopiperidine (4.27 g.) and triethylamine (3.5 g.) was refluxed in 100 ml. EtOH for 2 hours. The resulting yellow solution was cooled, whereupon the product crystallised . This was recrystallised twice from EtOH/-water to give the title compound (2.3 g.) as a pale yellow solid, m.p. 153° (dec.). Analysis : Calculated for $C_{30}H_{40}N_2O_2$; C, 78.22%; H, 8.75%; N, 6.08%. Found: C, 78.29%; H, 8.92%, N, 6.14%.

The product exhibits hypotensive activity in a standard test procedure.

EXAMPLE 67

7-[2-(4-Benzamidopiperid-1-yl)-1-hydroxyethyl]-1,1,3,4,4,6-Hexamethyl-1,2,3,4-tetrahydronaphthalene A solution of 7-(4-benzamidopiperidinoacetyl)-1,1,3,4,4,6-hexamethyl-1,2,3,4-tetrahydronaphthalene (10 g.) in methanol was cooled to 0°–10° C and treated with 1.1 g. sodium borohydride over ½–1 hour. The resulting solution was refluxed for 30 minutes, the solvent removed in vacuo, and the white solid residue treated with dilute HCl to give a flocculent white suspension, which was filtered off and recrystallised from EtOH/H$_2$O to give the title compound as the hydrochloride monohydrate 8.62 g. (78%), m.p. 253° (dec.). Analysis : Calculated for : $C_{30}H_{42}N_2O_2$.HCl H$_2$O : C, 69.64%; H, 8.77%; N, 5.41%. Found: C, 69.46%; H, 8.95%; N, 5.12%.

The product exhibited hypotensive activity.

EXAMPLE 68

1-[2-(2-Methoxyphenoxy)ethyl]-4-benzamidopiperidine 2-(2-Methoxyphenoxy)ethyl bromide (2.31 g.), 4-benzamidopiperidine (2.04 g.) and anhydrous potassium carbonate (1.38 g.) were well mixed and heated on a steam bath for 4 hr. The resulting mass was crushed and stirred in water (200 ml.) at 60° for 12 hr.

Filtration afforded the crude base of the title compound (2.95 g.). Conversion to the hydrochloride by solution in ethanol/HCl and precipitation with ether provided 3.01 g. of the title compound, as the hydrochloride m.p. 193.4°. Analysis : Found: C, 64.74; H, 7.08; N, 7.14. $C_{21}H_{26}N_2O_3$.HCl requires C, 64.52; H, 6.96; N, 7.17%.

The product exhibited hypotensive activity in a test procedure.

EXAMLE 69

4-Benzamido-1-(3-phenyl-3-oxopropyl)piperidine

4-Chloropropiophenone (3.37 g.) and 4-benzamidopiperidine (4.08 g.) were condensed in the presence of anhydrous potassium carbonate (2.76 g.) after the method of Example 68 to give the title compound as the hydrochloride (5.927 g.), m.p. 194.3° C. Analysis: Found: C, 67.52; H, 6.76; N, 7.75. $C_{21}H_{24}N_2O_2$. HCl requires C, 67.64; H, 6.76; N, 7.51%.

The product exhibited marked hypotensive activity in a standard test procedure.

EXAMPLE 70

4-Benzamido-1-[4-(4-tert-butyl-phenyl)-4-oxobutyl]-piperidine

4-Chloro-4'-tert-butylbutyrophenone (3.58 g.), 4-benzamidopiperidine (3.06 g.) and anhydrous potassium carbonate (2.67 g.) were reacted together in the manner of Example 68 to give the title compound (3.495 g.) as the hydrochloride, colourless microcrystals, m.p. 268.0°. Analysis: Found: C, 70.50; H, 8.14; N, 6.29. $C_{26}H_{34}N_2O_2$.HCl requires C, 70.48; H, 7.96; N, 6.32%.

The product exhibited hypotensive activity in a standard test procedure.

EXAMPLE 71

4-Benzamido-1-[4-(4-bromophenyl)-4-oxobutyl]-piperidine

4-Chloro-4'-bromobutyrophenone (2.61 g.), 4-benzamidopiperidine (2.04 g.) and anhydrous potassium carbonate (1.38 g.) were reacted together in the manner of Example 68 to give the title compound (3.34 g.) as the hydrochloride, colourless microcrystals, m.p. 268.0° . Analysis: Found: C, 57.11; H, 5.81; N, 5.92; $C_{22}H_{25}N_2O_2$.HCl requires C 56.72; H, 5.62; N, 6.02%.

The product exhibited hypotensive activity in a standard test procedure.

EXAMPLE 72

4-Amino-1-(4-phenyl-4-oxobutyl)piperidine

4-Benzamido-1-(4-phenyl-4-oxobutyl)piperidine (0.5 g.) was suspended in 6N HCl (10 ml.) and boiled for 8 hr. The solution was cooled, filtered (to remove benzoic acid) and the filtrate basified with potassium carbonate. The oil which separated was extracted into chloroform which on evaporation gave the title compound as the free base (0.30 g.). This was dissolved in ethanol, ethanol/HCl added until acid and the title compound filtered off (0.376 g.) as the dihydrochloride m.p. 269.7°.

Analysis: Found: C, 56.07; H, 7.53; N, 8.57. $C_{15}H_{22}N_2O$.2HCl requires C, 56.42; H, 7.58; N, 8.78%.

The product is useful as an intermediate for the corresponding 4-acylamido compound.

EXAMPLE 73

4-Amino-1-[2-(2-naphthyl)ethyl]-piperidine

4-Benzamido-1-[2-(2-naphthyl)ethyl]piperidine (1.0 g.) was suspended in 6N HCl (40 ml.) and boiled for 96 hr. The resulting solution was worked up in the manner of Example 72 to give the title compound (0.558 g.) as the dihydrochloride, pale yellow needles, m.p. >300° (decomp.)

Analysis: Found: C, 62.33; H, 7.26; N, 8.48. $C_{17}H_{22}N_2$.2HCl requires C, 62.38; H, 7.39; N, 8.56%.

The product is useful as an intermediate for the preparation of the corresponding 4-acylamido compounds.

EXAMPLE 74

4-Piperonylamido-1-(4-phenyl-4-oxobutyl)-piperidine

4-Amino-1-(4-phenyl-4-oxobutyl)piperidine dihydrochloride (3.19 g.) was stirred n chloroform (50 ml.). Water (20 ml.) containing potassium carbonate (8.28 g.) was added followed by dropwise addition of piperonyl chloride (1.84 g.) in chloroform (10 ml.). The mixture was stirred for 18 hr. Some of the title compound separated as the free base and was filtered off. The two-phase filtrate was separated and the remainder of the title compound (base) obtained. The combined bases were dissolved in ethanol/HCl and ether added until crystallisation occurred. Filtration afforded the title compound as the hydrochloride, three-quarter hydrate, colorless prisms (3.876 g.) m.p. 235.7°.

Analysis: Found: C, 62.19; H, 6.28; N, 6.33. $C_{23}H_{26}N_2O_4$.HCl.¾H$_2$O. C, 62.15; H, 6.47; N, 6.31%.

The product displayed hypotensive activity in a standard test procedure.

EXAMPLE 75

4-Cyclohexanecarboxamido-1-(4-phenyl-4-oxobutyl)-piperidine

4-Amino-1-(4-phenyl-4-oxobutyl)piperidine dihydrochloride (3.19 g.) was stirred in chloroform (50 ml.) and water (20 ml.) containing potassium carbonate (8.28 g.) in solution. Cyclohexylcarbonyl chloride (1.46 g.) in chloroform (10 ml.) was added dropwise and the mixture stirred 18 hr. Filtration afforded the title compound as the hydrochloride hemihydrate (1.89 g.). Recrystallisation (MeOH/Et$_2$O) afforded a purer product (1.46 g.), m.p. 230.8°.

Analysis: Found: C, 65.72; H, 8.46; N, 7.26. $C_{22}H_{32}N_2O_2.HCl.½H_2O$ requires C, 65.73; H, 8.53; N, 6.97%.

The product displayed marked hypotensive activity in a standard test procedure.

EXAMLE 76

4-(4-Chlorobenzamido)-1-(4-phenyl-4-oxobutyl)-piperidine

4-Amino-1-(4-phenyl-4-oxobutyl)piperidine dihydrochloride (3.19 g.) was acylated with p-chloro-benzoyl chloride (1.75 g.) in the manner of example 75. Filtration afforded the title compound as the base (3.277 g.). This was suspended in boiling ethanol (15 ml.) and ethanol/HCl added until acid. On cooling the title compound crystallised out as the hydrochloride, colourless needles (3.41 g.), m.p. 261.1°.

Analysis: Found: C, 62.89; H, 6.33; N, 6.64. $C_{22}H_{25}ClN_2O_2.HCl$ requires C, 62.69; H, 6.22; N, 6.65%.

The compound exhibited hypotensive activity in a standard test procedure.

EXAMPLE 77

4-Benzamido-1-[4-(4-methoxyphenyl)-4-oxobutyl]-piperidine

4-Benzamidopiperidine (4.086 g., 0.02 mole), 4-(4-chloro-1-oxobutyl)methoxybenzene (4.245 g., 0.02 mole) and finely ground anhydrous potassium carbonate (4.146 g., 0.03 mole) were mixed and heated on a steam bath for one hour. The solid obtained was stirred in water at 60° for one hour, the title compound was filtered off, washed well with water and ether to give 3.82 g. This was dissolved in hot absolute ethanol, the solution was acidified with ethanolic hydrogen chloride and cooled to give the hydrochloride of the title compound (3.54 g., 41%) m.p. 224.8°. $C_{23}H_{28}N_2O_3.HCl.H_2O$ requires C, 63.51; H, 7.18; N, 6.44. Found: C, 63.50; H, 6.84; N, 6.35%.

The product exhibited hypotensive activity in standard test procedures.

EXAMPLE 78

4-Benzamido-1-(1-phenylprop-2-yl)piperidine

4-Benzamidopiperidine (4.086 g., 0.02 mole), 2-bromo-1-phenyl-propane (4.978 g., 0.025 mole) and ground anhydrous potassium carbonate (4.146 g., 0.03 mole) were refluxed for 42 hours in 2-propanol (50 ml.). The hot mixture was filtered and the filtrate was evaporated to give a residue. This was stirred in water at 75° for one hour and the title compound was filtered off and washed with warm water and them with ether. Conversion to the hydrochloride as in Example 77 gave 2.193 g., (30.1%). m.p. 238.4° (dec.). $C_{21}H_{26}N_2O.HCl.¼H_2O$ requires C, 69.41; H, 7.63; N, 7.71. Found: C, 69.71; H, 7.73; N, 7.73%.

The product exhibited marked hypotensive activity in a standard test procedure.

EXAMPLE 79

1-[4-(1',2',3',4'-Tetrahydro-6'-naphthyl)-4-hydroxybutyl]-4-benzamidopiperidine 1-[4-(1',2',3',4'-tetrahydro-6'-naphthyl)-4-oxobutyl]-4-benzamidopiperidine (4.046 g., 0.01 mole) was dissolved in methanol (500 ml.) at 15° ml.) at 15° C, and while stirring a solution of sodium borohydride (10.0 g.) in 0.2 N sodium hydroxide solution (200 ml.) was added over 1 hour. The reaction mixture was stirred at room temperature for 20 hours, refluxed for 2 hours and filtered while hot. The methanol was distilled from the filtrate and the title compound crystallised out. This was converted to the hydrochloride by passing hydrogen chloride gas into a solution in methanol until acid and adding ethyl acetate and ether to precipitate the salt. The yield in two crops was 3.715 g., (84%) m.p. 238.9°. $C_{26}H_{34}N_2O_2.HCl.¼H_2O$ requires C, 69.79; H, 8.00; N, 6.26. C, 69.85; H, 8.12; N, 6.38%.

The product exhibited hypotensive activity in a standard test procedure.

EXAMPLE 80

1-[4-(2-Naphthyl)-4-oxobutyl]-4-benzamidopiperidine

4-Benzamidopiperidine (8.172 g., 0.04 mole) was alkylated with 4-chloro-1-(2'-naphthyl)butan-1-one (11.636 g.) using the procedure of Example 77, heating the reaction mixture at 100° for 2 hours. To the yellow solid was added water (300 ml.) and the crude title product was filtered off, washed with water, and then ether. The base obtained (7.561 g.) was converted to the hydrochloride as in Example 77 to yield 6.896 g., (40%), m.p. 250.6°. $C_{26}H_{28}N_2O_2.HCl.¾H_2O$ requires C, 69.33; H, 6.82; N, 6.22; Found: C, 69.60; H, 6.91; N, 6.10%.

The product exhibited hypotensive activity in a standard test procedure.

EXAMPLE 81

1-[4-(1',2',3',4'-Tetrahydro-6-naphthyl)butyl]-4-benzamidopiperidine

To a warm solution of 1-[4-(1',2',3',4'-tetrahydro-6'-naphthyl)-4-oxobutyl]-4-benzamidopiperidine (12.447 g.) in ethylene glycol (150 ml.) was added hydrazine hydrate (55 ml. of an 80% aqueous solution). The mixture was refluxed (liquid temperature 135°–40°) for 50 minutes. Potassium hydroxide pellets (6.0 g.) were added and the excess hydrazine and water were distilled off over 30 minutes during which time the temperature rose to 185°. Refluxing at this temperature was continued for a further 30 minutes. The hot mixture was poured into cold distilled water (500 ml.). and then allowed to stand at 0° overnight. An impure white solid was filtered off. This was converted to the hydrochloride as in Example 77 with the addition of ether to induce crystallisation After filtering off an impure first crop the concentrated mother liquor gave the title product as the hydrochloride, quarter hydrate, 1.965 g., (15%) m.p. 249.7°. $C_{26}H_{34}N_2O.HCl.¼H_2O$ requires C, 72.43; H, 8.29; N, 6.49. Found: C, 72.05; H, 8.10; N 6.35%.

The product exhibited hypotensive activity in a standard test procedure.

EXAMPLE 82

4-Benzamido-1-methyl-1-(4-phenyl-4-oxobutyl)-piperidinium iodide

A solution of 4-benzamido-1-(4-phenyl-4-oxobutyl)-piperidine (1.75 g., 0.005 mole) and iodomethane (7.10 g., 0.05 mole) in N,N-dimethylformamide (5 ml.) was stirred for 150 hours at room temperature. The reaction mixture was filtered and the residue was washed with fresh N,N-dimethylformamide and then diethyl ether.

The dried crude salt was recrystallised from water to give the title compound as square platelets (1.76 g., 71.5%) m.p. 271.8° (dec.). $C_{23}H_{29}IN_2O_2$ requires C, 56.10; H, 5.94; N, 5.70. Found: C, 56.19; H, 5.87; N, 5.57%.

The product exhibited hypotensive activity in a standard test procedure.

EXAMPLE 83

1-[4-(2'-Naphthyl)-4-hydroxybutyl]-4-benzamid-piperidine

Using the method of Example 79, 1-[4-(2'-naphthyl)-4-oxobutyl]-4-benzamidopiperidine (15.647 g.) was reduced to the title compound, obtained as the hydrochloride, hemihydrate (9.457 g., 54.0%) m.p. 241.3°. $C_{26}H_{30}N_2O_2.HCl.½H_2O$ requires C, 69.71; H, 7.20; N, 6.25. Found: C, 69.31; H, 7.00; N, 6.16%.

The product exhibited hypotensive activity in a standard test procedure.

EXAMPLE 84

4-Cyclohexane-carboxamido-1-[2-naphth-2-yl)ethyl]-piperidine

A solution of 4-amino-1-[2-(2'-naphthyl)ethyl]-piperidine (2.544 g., 0.01 mole) in chloroform (50 ml.) was stirred with an aqueous solution of potassium carbonate (2.764 g., 0.02 mole in 20 ml.). Over 5 minutes a solution of cyclohexane carbonyl chloride (1.466 g., 0.01 mole) in chloroform (10 ml.) was added and the reaction mixture was stirred overnight. The layers were separated, the aqueous one was washed with fresh chloroform, and the washings combined with the extract were dried ($MgSO_4$) and evaporated to give the title compound. This was converted to the hydrochloride as in Example 77 adding ether to induce crystallisation to yield 2.804 g., (70%) m.p. 232°–3°. $C_{24}H_{32}N_2O.HCl$ requires C, 71.91; H, 8.29; N, 6.99. Found; C, 71.77; H, 8.26; N, 6.94%.

The product exhibited hypotensive activity in a standard test procedure.

EXAMPLE 85

(−)4-Benzamido-1-(4-phenyl-4-hydroxybutyl)piperidine di-O,O-p-toluoyl tartrate 4-Benzamido-1-(4-phenyl-4-hydroxybutyl)piperidine (17.150 g.) and (−)-di-O,O-p-toluoyl tartaric acid (9.396 g. 0.5 equivalent) were dissolved in hot acetone. The solution was cooled overnight at 0° and filtered to give a white solid (17.195 g.). Five recrystallisations from acetone yielded 2,401 g. of a white salt, $[\alpha]_D = -45.49$. Two further crystallisations of this with no significant change in this value confirmed optically purity, $[\alpha]_d = -46.0$, m.p. 90°–100° (softens).

$C_{64}H_{74}N_4O_{12}$ requires C, 70.43; H, 6.84; N, 5.23. Found: C, 70.14; H, 6.99; N, 4.93%.

This product is an intermediate for the preparation of the compound of the next example.

EXAMPLE 86

(+)-4-Benzamido-1-(4-phenyl-4-hydroxybutyl)piperidine (−)-4-Benzamido-1-(4-phenyl-4-hydroxybutyl)-piperidine, di-O,O-p-toluoyl tartrate was dissolved in 0.5 N sodium hydroxide solution and extracted into chloroform. The dried extract was evaporated to give the title product, $[\alpha]_D=+16.17$. Two further crystallisations of the base yielded the title compound with a constant rotation, $[\alpha]_D=+15.3$ 1, m.p. 155°–6°. The optically pure base was converted to the hydrochloride m.p. 237.9°, in ethanolic hydrogen chloride and ether. $C_{22}H_{28}N_2O_2.HCl$ requires C, 67.95; H, 7.52; N, 7.20. Found: C, 68.13; H 7.44; N, 7.29%.

The product exhibits hypotensive activity in a standard test procedure.

EXAMPLE 87

4-(4-Benzamidopiperid-1-yl)-1,1-(di-p-fluorophenyl)-but-1-ene

Using the method of Example 77, 4-benzamidopiperidine (2.687 g.) was alkylated with 1,1-(di-p-fluorophenyl)-4-chlorobut-1-ene (3.784 g.) to give the title product as the hydrochloride, hemihydrate in 28% yield (1.821 g.) m.p. 272.7° C. $C_{28}H_{28}F_2N_2O.HCl.½H_2O$ requires C, 68.34; H, 6.15; N, 5.69. Found: C, 68.29; H, 6.19; N, 5.71%.

The product exhibits hypotensive activity and is an intermediate for the compound of the next example.

EXAMPLE 88

4-(4-Benzamidopiperid-1-yl)-1,1-(di-p-fluorophenyl)-butane 4-(4-Benzamidopiperid-1-yl)-1,1-(di-p-fluorophenyl)-but-1-ene, hydrochloride (885 mg.) was hydrogenated using 10% palladium charcoal (1.0 g.) at 50 p.s.i. and 50° in methanol (120 ml.) containing a few drops of concentrated hydrochloric acid for 24 hours. The catalyst was filtered off and the filtrate was evaporated to give a residue which gave the hydrochloride of the title compound (277 mg., 31.2%) m.p. 256.8°, on treatment with ethanolic hydrogen chloride and ether. $C_{28}H_{30}F_2N_2O.HCl$ requires C, 69.35; H, 6.44; N, 5.78. Found: C, 69.34; H, 6.79; H, 5.95%.

The product exhibited hypotensive activity in a standard test procedure.

EXAMPLE 89

4-(4-Benzamidopiperid-1-yl)-1,1-diphenylbut-1-ene

Using the procedure of Example 77 over a period of 20 hours, 4-benzamidopiperidine (7.473 g.) was alkylated with 1,1-diphenyl-4-chlorobut-1-ene (8.879 g.). The title compound was filtered off after addition of water and ether to the reaction mixture and a further crop was obtained from the ether washings. Conversion of the combined product to the hydrochloride using ethanolic hydrogen chloride gave 6.308 g. (38.2%). m.p. 220°–230° (dec.). $C_{28}H_{30}N_2O.HCl.¼H_2O$ requires C, 74.46; H, 7.03; N, 6.20. Found: C, 74.77; H, 7.26; N, 6.14%.

The product exhibited hypotensive activity in a standard test procedure and is an intermediate for the compound of the next example.

EXAMPLE 90

4-(4-Benzamidopiperid-1-yl)-1,1-diphenyl butane

Using the procedure of Example 88 4-(4-Benzamidopiperid-1-yl)-1,1-diphenylbut-l-ene (4.105 g., 0.01 mole) was reduced to the title compound using 500 mg. of 10 % palladium-charcoal. The hydrochloride of the product was obtained using the method of Example 77 in 62.4% yield (2.800 g.) m.p. 269.2°. $C_{28}H_{32}N_2O.HCl$ requires C, 74.90; H, 7.41; N, 6.24. Found: C, 74.55; H, 7.47; N, 6.15%.

The product exhibited hypotensive activity in a standard test procedure.

EXAMPLE 91

1-[3-(1,4-Benzodioxan-6-yl)-3-oxopropyl]-4-benzamidopiperidine

Using the procedure of Example 77, for a longer period of 20 hours, 4-benzamidopiperidine (1.022 g., 0.005 mole) was alkylated with 3-chloro-1-(1,4-benzodioxan-6-yl)propan-1-one (1.134 g., 1 equivalent) to give 1.433 g. of the crude base after washing with water and ether. Conversion of this to the hydrochloride by treatment with ethanolic hydrogen chloride and ether gave the title compound as the hydrochloride quarter hydrate (1.425 g., 65.5%) m.p. 198.1°. $C_{23}H_{26}N_2O_4.HCl.¼ H_2O$ requires C, 63.46; H, 6.37; N, 6.43; Found: C, 63.49; H, 6.57; N, 6.56%.

The product exhibited hypotensive activity in a standard test procedure.

EXAMPLE 92

1-[3-(1,4-Benzodioxan-6-yl)-3-hydroxypropyl]-4-benzamido piperidine

Using the procedure of Example 79 1-[3-(1,4-benzodioxan-6-yl)-3-oxopropyl]-4-benzamidopiperidine (5.918 g., 0.015 mole) was reduced to the title compound subsequently obtained as the hydrochloride (3.155 g., 48.6%) m.p. 193°-7°. $C_{23}H_{28}N_2O_4.HCl$ requires C,63.81; H, 6.75; N, 6.47. Found: C, 63.63; H, 6.89; H, 6.24%.

The product exhibited hypotensive activity in a standard test procedure.

EXAMPLE 93

1-[2-(4-Pyridyl)ethyl]-4-benzamidopiperidine

A mixture of 4-vinylpyridine (578 mg.), 4-benzamidopiperidine (1.02 g.), acetic acid (330 mg.) and methanol (5 ml.) was refluxed for 8 hours, cooled, and evaporated. The residue in water was basified with potassium carbonate and the resulting solid was collected. Recrystallisation from aqueous ethanol gave the product (1.24 g.) m.p. 193°-5° C. (Found: C, 73.3; H, 7.4; N, 13.3. $C_{19}H_{23}N_3O$ requires C, 73.75; H, 7.4; N, 13.3%.).

The product possessed marked hypotensive activity and also had antihistamine activity.

EXAMPLE 94

1-[2-(2-Pyridyl)ethyl]-4-benzamidopiperidine

A mixture of 2-vinylpyridine (5.78 g.), 4-benzamidopiperidine (10.20 g.) and acetic acid (3.30 g.) in methanol (50 ml.) was heated under reflux for 8 hours. The methanol was removed under reduced pressure, the residue was dissolved in water, cooled, and basified with potassium carbonate to precipitate the free base. The solid in ethanol was made just acid with ethanolic hydrogen chloride to give the title compound as the dihydrochloride, quarter hydrate (13.12 g.), m.p. 202°-3° C. (Found: C, 58.95; H, 6.6; N, 10.9. $C_{19}H_{23}N_3O.2HCl.¼ H_2O$ requires C, 59.0; H, 6.9; N, 10.9%).

The product exhibited marked hypotensive activity in a standard test. It also had antihistamine and depressant activities.

EXAMPLE 95

1-[2-(2-Quinolyl)ethyl]-4-benzamidopiperidine 2-(2-Hydroxyethyl)quinoline (5.0 g.) in thionyl chloride (15 ml.) was heated at 50° C. for 30 minutes. Excess thionyl chloride was removed and the residue was added to 4-benzamidopiperidine (4.74 g.) and potassium carbonate (12.0 g.) in dimethylformamide (25 ml.). The reaction mixture was stirred under reflux for 18 hours, cooled and shaken with water and ether. The ether extracts were dried and evaporated and the residue in acetonitrile was acidified with dry hydrogen chloride to give the product as the dihydrochloride, m.p. 198° C. (dec.). (Found: C, 63.7; H, 6.3; N, 9.7. $C_{23}H_{25}N_3O.2HCl$ requires C, 63.9; H, 6.3; N, 9.7%).

The product had marked hypotensive activity in a standard test.

EXAMPLE 96

1-[2-(4-Imidazolyl)ethyl]-4-benzamidopiperidine a. 4-Benzamidopiperidine (2.4 g.) in ethanol (15 ml.) was added to hydroxymethylvinyl ketone (2.0 g.). An exothermic reaction occurred and crystallisation occurred on cooling to give 2-(4-benzamidopiperidino) ethyl hydroxymethyl ketone, m.p. 154°-155° C. (Found: C, 65.9; H, 7.7; N, 9.5; $C_{16}H_{22}N_2O_3$ requires C, 66.2; H, 7.6; N, 9.65%).

b. The foregoing product (3.0 g.) in ethanol (10 ml.) was added to a mixture of cupric acetate (5g.), 0.880 ammonia (40 ml.) and 40% aqueous formaldehyde (3 ml.). The reaction mixture was heated on a steam bath for 1 hour. The copper salt was collected, suspended in hot water and brought to pH3. Hydrogen sulphide was passed in until there was no further precipitation then the mixture was filtered and the filtrate was evaporated. Trituration of the residue with ethanol gave the product as a dihydrochloride, hydrate, m.p. 228°-230° C. (Found: C, 52.45; H, 6.7; N 14.4. $C_{17}H_{22}N_4O.2HCl.H_2O$ requires C, 52.4; H, 6.7; N, 14.4%).

The product exhibited hypotensive activity and antihistamine activity.

EXAMPLE 97

1-(Pyrrole-2-yl)oxalyl-4-benzamidopiperidine

A solution of redistilled pyrrole (13.4 g.) in ether (50 ml.) was added to a stirred solution of oxalyl chloride (20 ml.) in ether (250 ml.) at −50° C. Stirring and cooling were maintained for 1 hour, then the solution was poured into a vigorously stirred mixture of sodium bicarbonate (100 g.) in water (600 ml.) and 4-benzamidopiperidine (80 g.) in chloroform (400 ml.). The reaction mixture was kept at 0° C for 40 hours, then the solid was filtered off and recrystallised from ethanol-water to give the product hydrate (80 g.), m.p. 124°–5° C. (Found: C, 63.0; H, 6.2; N, 12.2. $C_{18}H_{19}N_3O_3.H_2O$ requires C, 63.0; H, 6.2; N, 12.2%).

The product was useful as an intermediate for the next example.

EXAMPLE 98

1-[2-Hydroxy-2-(2-pyrrol-2-yl)ethyl]-4-benzamidopiperidine

The product of Example 97 (3.4 g.) in tetrahydrofuran (80 ml.) was added to a stirred suspension of lithium aluminium hydride (1.9 g.) in tetrahydrofuran (100 ml.). When the addition was complete the suspension was heated under reflux for 3 hours. Water (5.5 ml.) was added dropwise and the inorganic material was filtered off. Evaporation of the filtrate and recrystallisation of the residue from ethanol gave the product (2.5 g.) m.p. 138°–139° C. (Found: C, 69.1; H, 7.7; N, 13.2. $C_{18}H_{23}N_3O_2$ requires C. 69.0; H, 7.4: N, 13.4%).

The product exhibited hypotensive activity.

EXAMPLE 99

1-(2,5-Dimethyl-1-phenylpyrrol-3-yl-methyl)-4-benzamidopiperidine

A solution of 4-benzamidopiperidine (23.9 g.) in dioxan (200 ml.), acetic acid (200 ml.) and 40% aqueous formaldehyde (100 ml.) was cooled to 5° and a solution of 2,5-dimethyl-1-phenylpyrrole (20.0 g.) in dioxan (200 ml.) was added slowly with stirring. The mixture was stirred for 1 hr. at room temperature then 1 hr. at 70°. It was then extracted with diethylether. The aqueous layer was basified with 10N NaOH solution and extracted with chloroform. Evaporation of the washed and dried extracts gave a brown tar which partly solidified on standing 3 days. Trituration with diethylether and crystallisation from methanol-water gave the product as a hydrate (7.37 g.) m.p. 191°. (Found: C, 73.87; H, 7.53; N, 10.58. $C_{25}H_{29}N_3O.H_2O$ requires C, 74.04; H, 7.71; N, 10.36%).

The product exhibited hypotensive activity.

EXAMPLE 100

1-[2-(3-Benzo[b]thienyl)ethyl]-4-benzamidopiperidine a. 3-(2-Hydroxyethyl)benzo[b]thiophene (2.8 g.) in ahydrous pyridine (31 ml.) at −15° C. was stirred while p-toluenesulphonyl chloride (3.29 g.) was added portionwise. One hour later, water was added, keeping the temperature below −10° C. The aqueous layer was decanted off and the residual oil was dissolved in methanol and kept at 0° C. overnight, whereupon 3-(2-hydroxyethyl)benzo[b]thiophene, p-toluenesulphonate (1.71 g., m.p. 56°–8° C) crystallised. (Found: C, 61.3; H, 4.8. $C_{17}H_{16}O_3S_2$ requires C, 61.4; H, 4.85%).

b. A mixture of the foregoing tosylate (1.25 g.), 4-benzamidopiperidine (0.77 g.) and potassium carbonate (1.04 g.) in isopropanol (19 ml.) was heated under reflux for 17 hours. The hot reaction mixture was filtered and the filtrate was allowed to cool. The resulting crystals were recrystallised from ethanol made just acid with ethanolic hydrogen chloride to give the product hydrochloride hemihydrate, m.p. 242°–245° C. (Found: C, 64.4; H, 6.2; N, 7.1. $C_{22}H_{24}N_2OS.HCl.\frac{1}{2}H_2O$ requires C, 64.45; H, 6.4; N, 6.8%).

The product exhibited hypotensive activity and also antihistamine activity.

EXAMPLE 101

1-[2-(3-Benz[g]indolyl)ethyl]-4-benzamidopiperidine a. 4-Benzamidopiperidine (62 g.) was added to a stirred suspension of 1.1 g. cupric acetate and 9.5 g. paraformaldehyde in 300 ml. dry dioxane, followed by propiolaldehyde diethylacetal (38.6 g). Stirring was continued for 24 hours at 80° C under nitrogen. The hot reaction mixture was filtered and the filtrate was evaporated. Recrystallisation of the solid residue from ethyl acetatepetroleum ether (bp. 60°–80° C) gave 4-benzamido-1-(4,4-diethoxybut-2-ynyl)piperidine as colourless shining leaflets. (84.6 g.), m.p. 130° C. (Found: C, 69.5; H, 8.3; N, 8.3 $C_{20}H_{28}N_2O_3$ requires C, 69.7; H, 8.2; N, 8.1%).

b. The foregoing product (70 g.) in absolute ethanol (1 l.) was hydrogenated in the presence of 10% palladium-on-carbon (7 g.) at 50 p.s.i. hydrogen pressure for 30 minutes. Evaporation of the filtrate after removing the catalyst, and recrystallisation of the residue from petroleum ether (b.p. 60°–80° C) gave 1-(4,4-diethoxybutyl)-4-benzamidopiperidine as colourless leaflets (61.29 g.), m.p. 95° C. (Found: C, 69.0; H, 9.2; N, 8.2. $C_{20}H_{32}N_2O_3$ requires C, 68.9; H, 9.3; N, 8.0%).

c. 1-(4,4-Diethoxybutyl)-4-benzamidopiperidine (3.48 g.) was added portionwise to a solution of 1-naphthylhydrazine hydrochloride (1.95 g.) in 25% aqueous acetic acid (15 ml.) with stirring at 80° C. Stirring and heating were continued for 2.5 hours, then the mixture was left for 3 days at room temperature to precipitate the crude product (1.28 g.). Recrystallisation from ethanol gave the title compound as the hydrochloride, hemihydrate, m.p. 285° C (dec.). (Found: C, 70.2; H, 6.75; N, 9.2; $C_{26}H_{27}N_3O.HCl\frac{1}{2}H_2O$ requires C, 70.5; H, 6.6; N, 9.3%).

The product exhibited marked hypotensive activity. It also had depressant activity.

EXAMPLE 102

2-(4'-Benzamidopiperid-1-yl)methylbenzo-1,4-dioxan 2-(Bromomethyl)benzo-1,4-dioxan (4.58 g.) and 4-benzamidopiperidine (4.08 g.) were reacted in the presence of anhydrous potassium carbonate (2.76 g.) following the procedure of Example 37 to give the title compound as the hydrochloride (6.00 g.), m.p. 214.8° C. from ethanolic hydrogen chloride and ether. (Found: C, 64.7; H, 6.7; N, 7.15. $C_{21}H_{24}N_2O_3.HCl$ requires C, 64.85; H, 6.5; N, 7.2%).

The product had marked hypotensive activity and also prossesed anti-inflammatory activity.

EXAMPLE 103

| | |
|---|---|
| 1-[2-(2-Naphthyl)ethyl]-4-benzamidopiperidine, dihydrochloride | 10 mg. |
| Lactose | 77.5 mg. |
| Dried Maize Starch | 11.75 mg. |
| Magnesium Stearate | 0.75 mg. |

Tablets of the above composition were made by milling the active ingredient to 40 mesh (British Standard), sieving through a 40 mesh (British Standard) sieve, mixing the milled material with the other components, compressing to form tablets, regranulating, sieving to 20 mesh (British Standard) and then recompressing to form tablets.

EXAMPLE 104

| | |
|---|---|
| 1-[2-(2-Naphthyl)ethyl]-4-benzamidopiperidine, dihydrochloride | 2.5 mg. |
| Lactose | 157.34 mg. |
| Dried Maize Starch | 9 mg. |
| Alpine Talc | 9 mg. |
| Aerofil (Registered Trade Mark) | 1.8 mg. |
| Sodium Lauryl Sulphate | 0.36 mg. |

Capsules of the above were made up by thoroughly mixing together batches of the above ingredients, sieving to 40 mesh (British Standard) and filling hard gelatine capsules (180 mg.) with the mixture.

EXAMPLE 105

| | |
|---|---|
| 1-[2-(2-Naphthyl)ethyl]-4-benzamidopiperidine dihydrochloride | 4 mg. |
| Dextrose | 50 mg. |
| Water for injection | to 1 ml. |

Solutions suitable for injection were made up from the above ingredients and then filtered.

EXAMPLE 106

| | |
|---|---|
| 4-Benzamido-1-(4-phenyl-4-oxobutyl)-piperidine, hydrochloride, quarterhydrate | 10 mg. |
| Lactose | 77.5 mg. |
| Dried Maize Starch | 11.75 mg. |
| Magnesium Stearate | 0.75 mg. |

Tablets of the above composition were made by milling the active ingredient to 40 mesh (British Standard), sieving through a 40 mesh (British Standard sieve, mixing the milled material with the other components, compressing to form tablets, regranulating, sieving to 20 mesh (British Standard) and then re-compressing to form tablets.

EXAMPLE 107

| | |
|---|---|
| 4-Benzamido-1-[4-(4-chlorophenyl)-4-oxo-butyl]piperidine hydrochloride | 10 mg. |
| Lactose | 77.5 mg. |
| Dried Maize Starch | 11.75 mg. |
| Magnesium Stearate | 0.75 mg. |

Tablets of the above composition were made by milling the active ingredient to 40 mesh (British Standard), sieving through a 40 mesh (British Standard) sieve, mixing the milled material with the other components, compressing to form tablets, regranulating, sieving to 20 mesh (British Standard) and then recompressing to form tablets.

EXAMPLE 108

| | |
|---|---|
| 4-Benzamido-1-phenethylpiperidine | 10 mg. |
| Lactose | 77.5 mg. |
| Dried Maize Starch | 11.75 mg. |
| Magnesium Stearate | 0.75 mg. |

Tablets of the above composition were made by milling the active ingredient to 40 mesh (British Standard), sieving through a 40 mesh (British Standard, sieve), mixing the milled material with the other components, compressing to form tablets, re-granulating, sieving to 20 mesh (British Standard), and then recompressing to form tablets.

EXAMPLE 109

| | |
|---|---|
| 1-[2-(3,4-Dimethoxyphenyl)ethyl]-4-benzamidopiperidine | 10 mg. |
| Lactose | 77.5 mg. |
| Dried Maize Starch | 11.75 mg. |
| Magnesium Stearate | 0.75 mg. |

Tablets of the above composition were made by milling the active ingredient to 40 mesh (British Standard), sieving through a 40 mesh (British Standard) sieve, mixing the milled material with the other components, compressing to form tablets, re-granulating, sieving to 20 mesh (British Standard) and then recompressing to form tablets.

EXAMPLE 110

| | |
|---|---|
| 1-[3-Phenylpropyl]-4-benzamidopiperidine | 10 mg. |
| Lactose | 77.5 mg. |
| Dried Maize Starch | 11.75 mg. |
| Magnesium Stearate | 0.75 mg. |

Tablets of the above composition were made by milling the active ingredient to 40 mesh (British Standard), sieving through a 40 mesh (British Standard) sieve, mixing the milled material with the other components, compressing to form tablets, re-granulating, sieving to 20 mesh (British Standard) and then re-compressing to form tablets.

The above example is repeated replacing the active ingredient by 1-[3-phenylbutyl]-4-benzamidopiperidine.

It is to be understood that any other of the compounds of the invention in the form of the free base or a pharmaceutically acceptable salt or quaternary ammonium salt thereof, may be used in place of the active ingredient of Examples 103 – 110, especially the products of any of Examples 1, 6, 11, 14, 15, 16, 19, 20, 21, 24, 33, 35, 36, 40, 41, 42, 44, 45, 46, 47, 48, 49, 52–58, 63, 66, 67, 68, 69, 70, 74, 75, 76, 78, 79, 80, 81, 82, 83, 84, 86, 87–90, 91–96, 98–102.

The invention includes a method of relieving disorders and diseases of the cardiovascular system [and/or deep superficial allergic phenomena] in a mammal which comprises administering to said mammal a therapeutically effective amount of a heterocyclic compound of general formula (Ia)

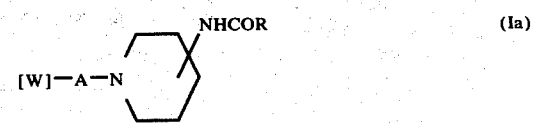

wherein W represents a cycloalkyl radical containing five to seven ring carbon atoms, a carbocyclic aryl radical, or a heterocyclic radical selected from pyridyl, pyrrolyl, imidazolyl, quinolyl, benzthienyl, benzodioxanyl, benzindolyl and radicals of the formula $Ar_2CHCH_2-$ and $Ar_2C=CH-$, wherein Ar is a phenyl radical, all of which W radicals may be substituted or unsubstituted, A represents a lower alkylene radical, a monoketo lower alkylene radical, a hydroxy-lower-alkylene radical or a bivalent radical of the formula —O—CH$_2$CH(OH)CH$_2$— or —O—(lower alkylene)—, R represents a substitiuted or unsubstituted phenyl radical or a cycloalkyl radical containing from 5 to 7 ring carbon atoms, the term "lower" means that the radical contains from 1 to 6 carbon atoms, and the pharmaceutically acceptable acid addition salts thereof with the proviso that when W is Ar$_2$CHCH$_2$— or ArC:-CH— then A is a lower alkylene radical of 1 to 4 carbon atoms.

In a preferred aspect a compound used in the above method is one in which W is cyclohexyl, phenyl, monohalophenyl, dihalophenyl, lower alkoxyphenyl, dilower alkoxyphenyl, trilower alkoxyphenyl, lower alkylphenyl, di-(loweralkyl)phenyl, hydroxphenyl, dihydroxyphenyl, methylenedioxyphenyl, ethylenedioxyphenyl, lower alkanoylaminophenyl, nitrophenyl, aminophenyl, di-(loweralkyl)aminophenyl or acetylaminohydroxyphenyl, A is lower alkylene of 1 to 6 preferably 2 - 4 carbon atoms or W—A is Ar$_2$CHCH$_2$(CH$_2$)$_n$ or Ar$_2$C=CH$_2$ (CH$_2$)$_n$ where Ar is phenyl or halophenyl and $n$ is an integer from 1 to 4.

Tests for action on the cardiovascular system were conducted according to one of the following procedures:

Hypotensive and/or Anti-Hypertensive activity

Method 1 (RAT)

Rats were anaesthetised with pentobarbitone sodium (60 mg/kg) and the jugular vein, trachea and carotid artery were cannulated. The test compound was given intravenously at 15 minute intervals (dose range 0.8–25.6 mg/kg cumulative) and blood pressure and heart rate were recorded via the carotid artery at 30 seconds and 15 minutes after administration. The production of a fall of 30 mm. mercury or more in diastolic pressure from control values was considered to be significant hypotensive activity. A decrease in heart rate of more than 30% from control values was considered to be significant bradycardia.

Results obtained for a few compounds of the invention were:

| Compound | Result |
|---|---|
| 1) 1-Phenethyl-4-benzamido piperidine | Significant hypotension 3.2 mg/kg Significant bradycardia 3.2–12.8 mg/kg. Fatal 12.8–25.6 mg/kg. |
| 2) 1-[4-(4-fluorophenyl)-4-oxobutyl]-4-benzamido-piperidine | Significant hypotension 0.8–1.6 mg/kg. Significant bradycardia 1.6 mg/kg. |
| 3) 1-[3-phenylpropyl]-4-benzamidopiperidine | Significant hypotension 0.8–6.4mg/kg Significant bradycardia 25.6 mg/kg |
| 4) 4-Benzamido-1-(4-phenyl-4-oxobutyl)piperidine | Significant hypotension 0.8–1.6mg/kg Significant bradycardia 0.8–1.6mg/kg |
| 5) 1-[4-p-fluorophenyl)-4-hydroxybutyl]-4-benz amidopiperidine | Significant hypotension 6.4–12.8 mg/kg Significant bradycardia 6.4–12.8 mg/kg |

Method 1 (Cat)

Cats were anaesthetised with pentobarbitone sodium (30 mg/kg) and the cephalic vein, femoral and carotid arteries and trachea were cannulated. The carotid cannula was introduced into the left ventricle and the femoral cannula into the aorta. Blood pressure and heart rate were recorded from the aortic cannula and left ventricular pressure from the carotid cannula. The test compunds were administered intravenously (0.1–25.6 mg/kg).

The following result was obtained with compound 2 above.

Significant lowering of blood pressure (38 mmHg) at 3.2 mg/kg. At this dose myocardial contractile force decreased by 25.7% and heart rate lowered by 28.9% cardiac output was decreased and cardiac effort index was also lowered.

The following result was obtained with compound 4 above.

Significant lowering of blood pressure (52 mmHg) at 3.2 mg/kg. At this dose level myocardial contractile force decreased by 33% and heart rate was lowered by 35%. Cardiac output and cardiac effort index were also lowered.

Method 2 (hypertensive rats)

Male or female rats are rendered hypertensive by applying a figure of 8 ligature around one kidney and contralateral nephrectomy. Blood pressure stabilises at a hypertensive level after 6 weeks. Systolic pressure is measured indirectly using a Decker Caudal Plethysmograph A control group of rats is run with each group treated with drug. Each group usually consists of six rats. Drugs are usually administered by the IP or oral routes. Pressures are read prior to drug administration and at two and 24 hours thereafter.

| Compound | Result |
|---|---|
| Compound 2 above | Pressure reduced from 188 to 138 mmHg at 10 mg/kg p.o. |
| Compound 4 above | Pressure reduced from 174 to 122 mmHg at 40 mg/kg p.o. |
| Compound 5 above | Pressure reduced from 209 to 164 mmHg at 10 mg/kg. Toxic at 40 m.p.k. |

α-Adrenoceptor Antagonism Activity

Carried out on the guinea pig aortic strip [Furchgott and Bhadrakom (1953) J. Pharmac. exp. Ther. 108, 129–143] by the method of Alps et al [Br. J. Pharmac. 1972 44, 52–62].

The following results were obtained with some compounds of the invention:

| Compound | pA$_2$ | Number of Experiments |
|---|---|---|
| Compound 1 above | 5.7 | 2 |
| Compound 2 above | 7.4 | 4 |
| Compound 3 above | 7.1 | 2 |
| Compound 4 above | 7.7 | 3 |
| Compound 5 above | 6.6 | |

Antihistamine activity was determined by the method of Alps et al. [Br. J. Pharmacol. 1972, 44, 52–62].

The following results were obtained with some compounds of the invention:

Table 2

| Compound | pA$_2$ | Number of Experiments |
|---|---|---|
| Compound 1 above | 7.1 | 2 |
| Compound 2 above | 8.6 | 4 |
| Compound 3 above | 8.5 | 4 |
| Compound 4 above | 9.5 | 8 |
| Compound 5 above | 6.5 | 2 |

Activity in either method 1 (rats or cats) or method 2 was considered to indicate hypotensive activity.

The above results and further test results are summarised in the following tables:

Table 3

| Compound of Example | Hypotensive Activity$^a$ | Anti-hypertensive Activity$^b$ |
|---|---|---|
| 1 | +++ | +++g |
| 5 | ± | +++ |
| 6 | + | |
| 7 | ± | ± |
| 8 | ++ | +g |
| 9 | ± | ±g |
| 10 | ++ | ± |
| 11 | +++ | + |
| 12 | ± | |
| 13 | +++ | + |
| 14 | ++ | |
| 15 | ++ | +++ |
| 17 | ± | |
| 18 | ± | |
| 19 | ++++ | ++h |
| 20 | ++ | ++g |
| 21 | ++ | ± |
| 22 | + | ± |
| 23 | ± | ± |
| 24 | ++ | ++ |
| 27 | +++ | |
| 30 | + | |
| 32 | ± | |
| 33 | ++ | ++g |
| 34 | ± | |
| 35 | ++ | +++ |
| 36 | ± | ± |
| 37 | +++ | + |
| 38 | ± | ± |
| 39 | ++ | |
| 40 | +++ | +i |
| 41 | ++ | + |
| 43 | ++++ | +++ |
| 44 | +++ | ± |
| 45 | +++ | ± |
| 46 | ++ | + |
| 47 | + | ++ |
| 48 | ++ | ++ |
| 49 | ++ | ± |
| 50 | ++ | |
| 51 | ++ | + |
| 52 | ++ | +++ |
| 53 | ++ | ++ |
| 54 | ++ | ++ |
| 55 | +++ | + |
| 56 | ++ | ± |
| 57 | +++ | ± |
| 58 | +++ | ± |
| 63 | + | + |
| 64 | ± | ± |
| 65 | + | ± |
| 66 | ++ | |
| 67 | +(+) | ++ |
| 68 | ++ | ± |
| 69 | +++ | +++ |
| 70 | ++++ | ± |
| 71 | + | ± |
| 74 | ++ | ± |
| 75 | ++ | +++ |
| 76 | ++ | + |
| 77 | ++ | ++ |
| 78 | ++ | +++ |
| 79 | +++ | ± |
| 80 | +++ | + |
| 81 | +++ | + |
| 83 | +++ | + |
| 84 | ++ | ± |
| 86 | +++ | |
| 87 | + | |
| 88 | +++ | + |
| 89 | ++ | + |

Table 3-continued

| Compound of Example | Hypotensive Activity$^a$ | Anti-hypertensive Activity$^b$ |
|---|---|---|
| 90 | ++ | + |
| 91 | + | |
| 92 | +++ | + |
| 93 | ± | +++ |
| 94 | +(+) | +++ |
| 95 | ++(+) | |
| 96 | ++ | + |
| 98 | ++(+) | ± |
| 99 | ± | ++ |
| 100 | ± | +++ |
| 101 | ++ | +++ |

Key: a Cumulative iv doses producing a fall in diastolic blood pressure of 30 mm or more, sustained for at least 15 min: 0.8 mg/kg, ++++; 1.6 or 3.2 mg/kg, +++; 6.4 or 12.8 mg/kg, ++; 25.6 mg/kg, +. Falls of <30mm, ±. b Falls in systolic blood pressure 2 hr after an oral dose of 40 mg/kg: >50 mm, +++; 50–30mm, ++; 30–15 mm, +; <15 mm, ±. g Oral dose of 75 mg/kg. h Oral dose of 10 mg/kg. i Oral dose of 2.5 mg/kg.

TABLE 4

| Example | α-blockade pA$_2$ | Antihistamine pA$_2$ |
|---|---|---|
| 10 | 5.8 | |
| 13 | 7.4 | 7.6 |
| 15 | 7.4 | |
| 17 | | 7.0 |
| 19 | 7.5 | 8.6 |
| 20 | 6.6 | |
| 27 | | 7.1 |
| 37 | 7.35 | 8.4 |
| 39 | 7.1 | 8.6 |
| 40 | 6.4 | 7.5 |
| 43 | 7.7 | 9.6 |
| 44 | 7.5 | 7.7 |
| 45 | 7.2 | 8.0 |
| 46 | 6.95 | 7.4 |
| 51 | 8.4 | 7.7 |
| 52 | 5.9 | |
| 54 | 6.6 | 6.5 |
| 58 | 6.9 | |
| 63 | 7.0 | 8.9 |
| 69 | 6.6 | |
| 70 | 6.6 | |
| 72 | 6.9 | |
| 74 | 6.4 | |
| 75 | 6.9 | |
| 79 | 6.05 | 7.0 |
| 81 | 6.6 | |
| 88 | 5.9 | |
| 92 | 6.6 | |

We claim:

1. A pharmaceutical composition for use in the treatment of hypertension comprising dosage form of a non-toxic pharmaceutically acceptable solid carrier and an effective amount of a heterocyclic compound of general formula (Ia),

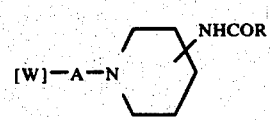

wherein W is phenyl, mono-halophenyl, dihalophenyl, (lower)alkoxyphenyl, di(lower)alkoxyphenyl, tri(lower)alkoxyphenyl, (lower)alkylphenyl, di-(lower)alkylphenyl, hydroxyphenyl, dihydroxyphenyl, methylenedioxyphenyl, ethylenedioxyphenyl, lower alkanoylaminophenyl, nitrophenyl, aminophenyl, di-(loweralkyl)-aminophenyl or acetylaminohydroxyphenyl; A is alkylene of 1–6 carbon atoms; and R is phenyl, or a pharmaceutically acceptable acid addition salt thereof, said unit dosage being in the form of a powder, capsule or tablet.

2. A pharmaceutical composition of claim 1 in which said heterocyclic compound is:

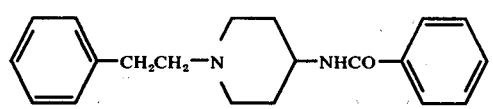

or a pharmaceutically acceptable acid addition salt thereof.

3. A pharmaceutical composition of claim 1 in which said heterocyclic compound is:

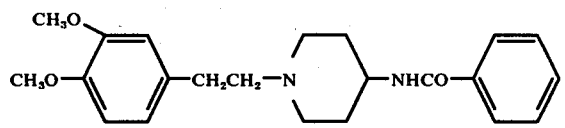

or a pharmaceutically acceptable acid addition salt thereof.

4. A pharmaceutical composition of claim 1 in which said heterocyclic compound is:

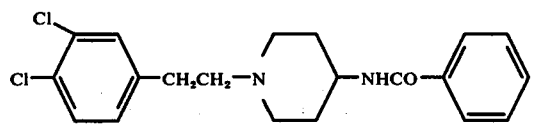

or a pharmaceutical acceptable acid addition salt thereof.

5. A pharmaceutical composition of claim 1 in which said heterocyclic compound is:

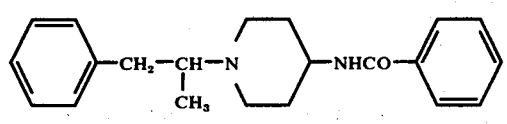

or a pharmaceutical acceptable acid addition salt thereof.

6. A pharmaceutical composition of claim 1 in which said heterocyclic compound is:

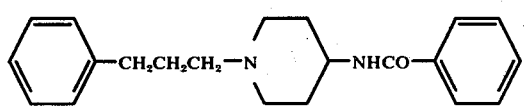

or a pharmaceutically acceptable acid addition salt thereof.

7. A pharmaceutical composition of claim 1 in which said heterocyclic compound is:

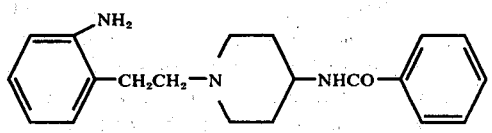

or a pharmaceutically acceptable acid addition salt thereof.

8. A pharmaceutical composition of claim 1 in which said heterocyclic compound is:

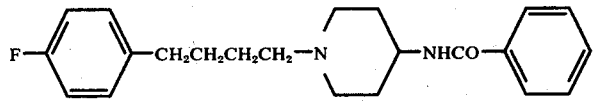

or a pharmaceutically acceptable acid addition salt thereof.

9. A method for the treatment of hypertension in a mammal which comprises administering to said mammal a therapeutically effective amount of a heterocyclic compound of general formula (Ia)

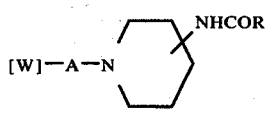

wherein W is phenyl, mono-halophenyl, dihalophenyl, lower alkoxyphenl, di(lower)alkoxyphenyl, tri(lower) alkoxyphenyl, (lower)alkylphenyl, di-(lower)alkylphenyl, hydroxyphenyl, dihydroxyphenyl, methylenedioxyphenyl, ethylenedioxyphenyl, lower alkanoylaminophenyl, nitrophenyl, aminophenyl, di-(loweralkyl)-aminophenyl or acetylaminohydroxyphenyl; A is alkylene of 1-6 carbon atoms; and R is phenyl, or a pharmaceutically acceptable acid addition salt thereof.

10. A method of claim 9 in which said heterocyclic compound administered is:

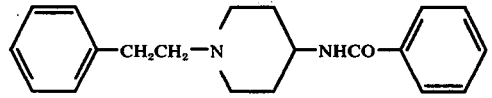

or a pharmaceutically acceptable acid addition salt thereof.

11. A method of claim 9 in which said heterocyclic compound administered

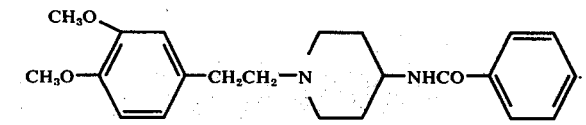

12. A method of claim 9 in which said heterocyclic compound administered is:

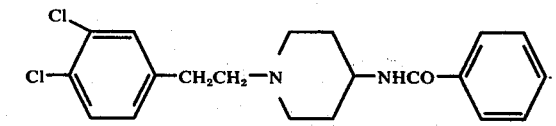

13. A method of claim 9 in which said heterocyclic compound administered is:

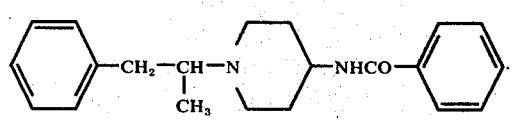

14. A method of claim 9 in which said heterocyclic compound administered is:
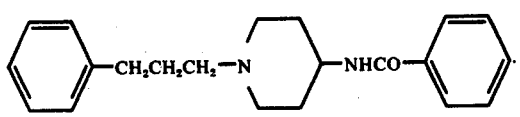
15. A method of claim 9 in which said heterocyclic compound administered is:
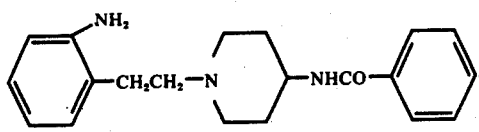
16. A method of claim 9 in which said heterocyclic administered is:
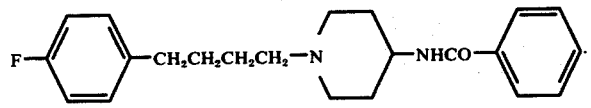
* * * * *